United States Patent
Luman et al.

(10) Patent No.: US 12,365,873 B2
(45) Date of Patent: Jul. 22, 2025

(54) METHODS FOR TRANSDUCING IMMUNE CELLS

(71) Applicant: Allogene Therapeutics, Inc., South San Francisco, CA (US)

(72) Inventors: Todd Luman, Hayward, CA (US); Josergio Zaragoza, Daly City, CA (US); Abraham Germansderfer, Boca Raton, FL (US); Suma Rao, San Francisco, CA (US); Yajin Ni, San Diego, CA (US); Chupei Zhang, San Francisco, CA (US); Tom Tao Huang, Fremont, CA (US)

(73) Assignee: Allogene Therapeutics, Inc., South San Francisco, CA (US)

( * ) Notice: Subject to any disclaimer, the term of this patent is extended or adjusted under 35 U.S.C. 154(b) by 108 days.

(21) Appl. No.: 17/587,138

(22) Filed: Jan. 28, 2022

(65) Prior Publication Data

US 2022/0249556 A1 Aug. 11, 2022

Related U.S. Application Data

(60) Provisional application No. 63/302,225, filed on Jan. 24, 2022, provisional application No. 63/142,730, filed on Jan. 28, 2021.

(51) Int. Cl.
| | | |
|---|---|---|
| C12N 5/0783 | (2010.01) | |
| A61K 40/11 | (2025.01) | |
| A61K 40/31 | (2025.01) | |
| A61K 40/40 | (2025.01) | |
| C12N 15/86 | (2006.01) | |

(52) U.S. Cl.
CPC ............ *C12N 5/0636* (2013.01); *A61K 40/11* (2025.01); *A61K 40/31* (2025.01); *A61K 40/40* (2025.01); *C12N 15/86* (2013.01); *C12N 2740/15041* (2013.01)

(58) Field of Classification Search
CPC .... A61K 35/17; A61K 39/0011; C12N 15/86; C12N 5/0636; A61P 35/00
USPC .............................................. 424/93.71, 93.2
See application file for complete search history.

(56) References Cited

U.S. PATENT DOCUMENTS

| | | | |
|---|---|---|---|
| 5,827,642 | A | 10/1998 | Ridell et al. |
| 6,040,177 | A | 3/2000 | Ridell et al. |
| 6,319,494 | B1 | 11/2001 | Capon et al. |
| 6,797,514 | B2 | 9/2004 | Brenson et al. |
| 6,867,041 | B2 | 3/2005 | Berenson et al. |
| 6,905,874 | B2 | 6/2005 | Berenson et al. |
| 7,709,226 | B2 | 5/2010 | Foote |
| 7,741,465 | B1 | 6/2010 | Eshhar et al. |
| 10,125,352 | B2 | 11/2018 | Fenard |
| 10,465,169 | B2 | 11/2019 | Boudeffa et al. |
| 2011/0286980 | A1 | 11/2011 | Brenner |
| 2012/0201794 | A1 * | 8/2012 | Chen ............... C12N 15/1138 435/325 |
| 2017/0296678 | A1 | 10/2017 | Frost et al. |
| 2019/0367876 | A1 | 12/2019 | Frost et al. |

FOREIGN PATENT DOCUMENTS

| | | | |
|---|---|---|---|
| EP | 2829285 B1 | 10/2017 | |
| WO | 2012079000 A1 | 6/2012 | |
| WO | 2012129514 A1 | 9/2012 | |
| WO | 2013153391 A1 | 10/2013 | |
| WO | 2015120096 A2 | 8/2015 | |
| WO | 2016120216 A1 | 8/2016 | |
| WO | WO-2017173410 A1 * | 10/2017 | ............. A61K 35/17 |
| WO | 2018136570 A9 | 7/2018 | |
| WO | 2018161064 A1 | 9/2018 | |

OTHER PUBLICATIONS

Jensen et al. "Small increases in pH enhance retroviral vector transduction efficiency of NIH-3T3 cells". Biotechnol Prog. Jan.-Feb. 2003;19(1):216-23. (Year: 2003).*
Al-Lazikani, Bissan, et al., "Standard Conformations for the Canonical Structures of Immunoglobulins", J. Mol. Biol. (1997) 273, 927-948.
Chothia, Cyrus, et al., "Canonical structures for the hypervariable regions of immunoglobulins", J Mol Biol; Aug. 20, 1987;196(4):901-17. doi: 10.1016/0022-2836(87)90412-8.
Coffin, John M., et al., "Retroviruses", Cold Spring Harbor Laboratory Press; 1997 (TOC) ; https://www.ncbi.nlm.nih.gov/books/NBK19376/.
Denning, Warren, et al., "Optimization of the transductional efficiency of lentiviral vectors: effect of sera and polycations", Mol Biotechnol; . Mar. 2013;53(3):308-14. doi: 10.1007/s12033-012-9528-5.
EPO, "International Search Report & Written Opinion", mailed on Jul. 12, 2022 for International Application No. PCT/US2022/014247.
Finney, Helen, et al., "Chimeric Receptors Providing Both Primary and Costimulatory Signaling in T Cells from a Single Gene Product", J Immunol Sep. 15, 1998, 161 (6) 2791-2797.
Gross, Gideon, et al., "Therapeutic Potential of T Cell Chimeric Antigen Receptors (CARs) in Cancer Treatment: Counteracting Off-Tumor Toxicities for Safe CAR T Cell Therapy", Annual Review of Pharmacology and Toxicology; vol. 56:59-83 (Volume publication date Jan. 2016) https://doi.org/10.1146/annurev-pharmtox-010814-124844.
Jensen, T. W., et al., "Small increases in pH enhance retroviral vector transduction efficiency of NIH-3T3 cells", Biotechnol Prog; . Jan.-Feb. 2003; 19(1):216-23. doi: 10.1021/bp025604g.

(Continued)

*Primary Examiner* — Allison M Fox
*Assistant Examiner* — Hanan Isam Abuzeineh
(74) *Attorney, Agent, or Firm* — Allogene Therapeutics, Inc.

(57) ABSTRACT

Provided herein are improved methods for transducing immune cells, such as T cells, with retroviral vectors to express exogenous gene products, such as chimeric antigen receptors (CARs). Provided herein are methods that increase transduction efficiency thereby increasing the percentage of immune cells in a population expressing the exogenous gene product. Associated cells, cell populations, compositions and methods of use are also provided.

29 Claims, 4 Drawing Sheets

(56) References Cited

OTHER PUBLICATIONS

Kabat, Elvin A., et al., "Sequences of Proteins of Immunological Interest", 5th Ed. NIH publication, No. 91-3242; 1992 (TOC).

Kalos, Michael, et al., "T Cells with Chimeric Antigen Receptors Have Potent Antitumor Effects and Can Establish Memory in Patients with Advanced Leukemia", Science Transnational Medicine, vol. 3 Issue 95 95ra73, 2011.

NCBI, "HIV-1, complete genome", GenBank: AF033819.3.

NCBI, "*Homo sapiens* CD28 molecule (CD28), mRNA", NCBI Reference Sequence: NM_006139.1.

NCBI, "*Homo sapiens* TNF receptor superfamily member 9 (TNFRSF9), mRNA", NCBI Reference Sequence: NM_001561.5.

NCBI, "T-cell surface glycoprotein CD8 alpha chain isoform 1 precursor [*Homo sapiens*]", NCBI Reference Sequence: NP_001139345.1.

NCBI, "T-cell-specific surface glycoprotein CD28 isoform 1 precursor [*Homo sapiens*]", NCBI Reference Sequence: NP_006130.1.

NCBI, "Tumor necrosis factor receptor superfamily member 9 precursor [*Homo sapiens*]", NCBI Reference Sequence: NP_001552.2.

Paugh, Barbara S., et al., "Reference standards for accurate validation and optimization of assays that determine Integrated lentiviral vector copy number in transduced cells", Scientific Reports; (2021) 11:389; DOI https://doi.org/10.1038/s41598-020-79698-w.

Porter, David L., et al., "Chimeric Antigen Receptor-Modified T Cells in Chronic Lymphoid Leukemia", N Engl J Med 2011;365:725-33.

Song, De-Gang, et al., "CD27 costimulation augments the survival and antitumor activity of redirected human T cells in vivo", Blood (2012) 119 (3): 696-706.

Tramontano, Anna, et al., "Framework Residue 71 is a Major Determinant of the Position and Conformation of the Second Hypervariable Region in the V H Domains of Immunoglobulins", J. Mol. Biol. (1990) 215, 175-182.

* cited by examiner

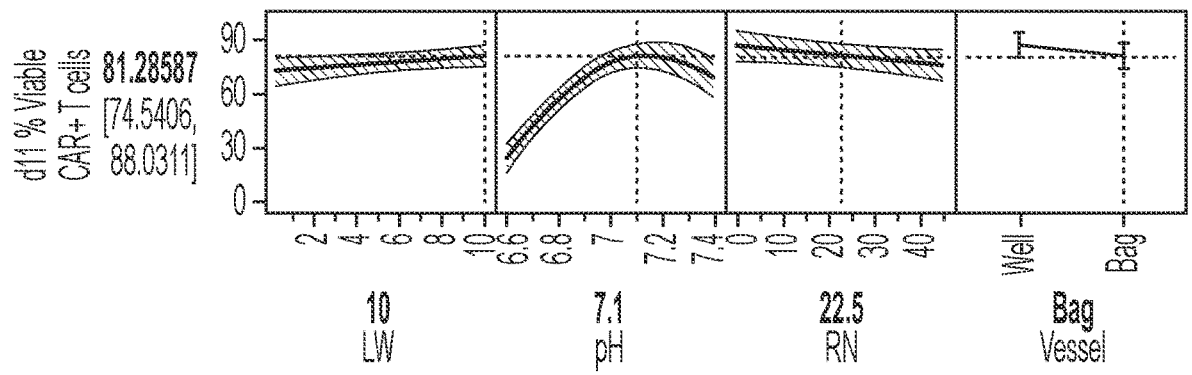
FIG. 2A
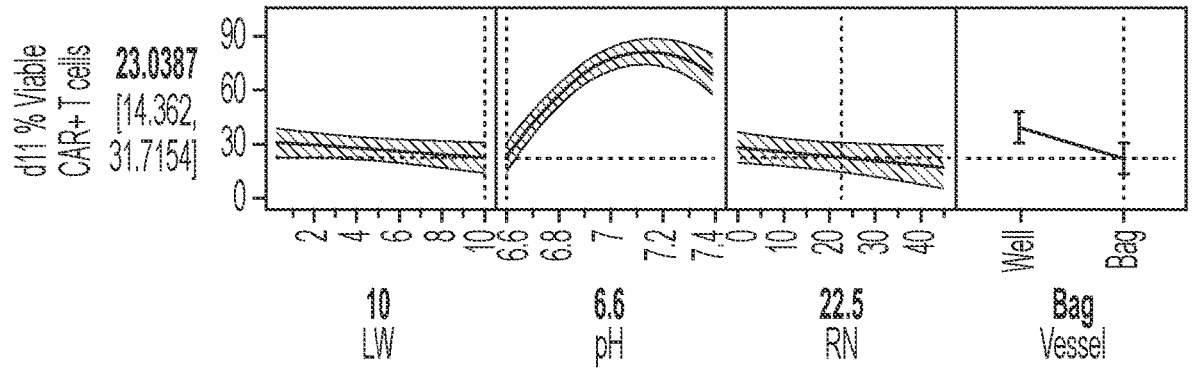
FIG. 2B
| Source | LogWorth | | PValue | |
|---|---|---|---|---|
| pH*pH | 3.764 | | 0.00017 | |
| pH(6.6,7.4) | 3.256 | | 0.00056 | ^ |
| LW(0.25,10) | 2.758 | | 0.00175 | |
| LW*pH | 2.311 | | 0.00489 | |
| LW*Vessel | 2.284 | | 0.00520 | |
| pH*Vessel | 1.673 | | 0.02123 | |
| Vessel | 1.458 | | 0.03484 | ^ |
| RN*Vessel | 1.364 | | 0.04322 | |
| RN(0,45) | 0.621 | | 0.23940 | ^ |
FIG. 2C

METHODS FOR TRANSDUCING IMMUNE CELLS

CROSS REFERENCE TO RELATED APPLICATIONS

The present application claims the benefit of priority to U.S. Provisional Application No. 63/142,730, filed Jan. 28, 2021; and U.S. Provisional Application No. 63/302,225, filed Jan. 24, 2022, the contents of both of which are hereby incorporated by reference in their entireties.

FIELD OF DISCLOSURE

This disclosure relates to methods for transducing immune cells, such as T cells, with a retroviral vector to express a gene product, such as a chimeric antigen receptor (CAR) gene product.

BACKGROUND OF THE DISCLOSURE

In adoptive cell therapy, autologous and allogeneic immune cells can be genetically modified to express synthetic proteins that enable the cells to perform new therapeutic functions. Immune cells can be genetically engineered to express chimeric antigen receptors ("CARs"), fusion proteins comprised of an antigen recognition moiety and T cell activation domains. The engineered immune cells that contain CARs, e.g., CAR-T cells ("CAR-Ts"), have antigen specificity and a retained or enhanced ability to recognize and kill a target cell, such as a cancer cell. The immune cells can be engineered by transduction in which a nucleic acid encoding a CAR is introduced into the immune cell via a viral vector. Prior methods of transducing immune cells for CAR T immunotherapy, particularly transducing allogeneic immune cells at the manufacturing scale, can be inefficient, produce inconsistent results and commonly use reagents that drive up processing costs and complexity.

Thus, there remains a need for a method of producing CAR-T cells in which immune cell transduction efficiency is both robust and consistent and is simpler and less expensive than the current methods.

SUMMARY

Described herein are improved methods for transducing immune cells with a viral vector providing a genetically modified population of immune cells having a higher percentage of cells expressing an exogenous gene product, cell populations comprising a higher percent of exogenous gene product positive cells, and methods of treatment employing populations of cells prepared using the disclosed methods. Further, the described methods provide genetically modified cell populations having a more consistent percentage of cells expressing an exogenous gene product from production run to production run, and/or less expensive and less complex transduction methods. For example, described herein are methods that are particularly suitable for T cell retroviral vector transduction, which can be used for the manufacture of cells useful in allogenic cell therapies employing chimeric antigen receptors (e.g., allogeneic CAR-T cell therapy).

In one aspect, a method for transducing a population of cells with a retroviral vector where the vector comprises a nucleic acid exogenous to the cells, the method comprising a) selecting the cell population, wherein the selected cell population comprises T lymphocytes, helper T cells, tumor cells, memory T cells, cytotoxic T cells, natural killer T cells, peripheral blood lymphocytes, peripheral blood mononuclear cells, dendritic cells, or natural killer cells or mixtures thereof, and b) culturing the selected cell population with the retroviral vector, in a cell culture media at starting pH in a starting pH range of 7.0 to 7.9 and maintaining the starting pH in the starting pH range for at least the first hour of the transduction culturing step to result in a transduced cell population comprising cells expressing a gene product encoded by the exogenous nucleic acid, is provided.

In one embodiment, the starting pH of the transduction method is maintained in a starting pH range of 7.0 to 7.9 for at least 1, 2, 4, 6, 8, 10, 12, 16, 18, 20, 22 or 24 hours. In some embodiments, the starting pH is maintained in the starting pH range for at least about 1, about 2, about 4, about 6, about 8, about 10, about 12, about 14, about 16, about 18, about 20, about 22, about 24, about 36, about 48, about 72 or about 96 hours to no more than about 168 hours.

In some embodiments, the starting pH is maintained in the starting pH range through the end of the transduction culturing step. In some embodiments, the transduction culturing step is conducted for at least 1, 2, 4, 6, 8, 12, 14, 16, 18, 20, 22, 24, 36, 48, 72 or 96 hours. In some embodiments, the pH is controlled passively. In some embodiments, the pH is controlled actively with a bioreactor.

In some embodiments, the transduction method of the instant disclosure comprises culturing the selected cell population at a MOI of about 0.25, about 0.5, about 1, about 5, about 10, about 15, about 20, about 25, about 30, about 35, about 40, about 45, about, or about 50 to about 55, about 60, about 65, about 70, about 75, about 80, about 85, about 90, about 95, about 100, about 125, about 150, about 175, about 200, about 225, or about 250. In some embodiments the MOI is a ratio of functional viral particles to total number of target cells in a transduction procedure. In some embodiments, the titer of the functional viral particles to be added to a transduction procedure is determined by qPCR.

In some embodiments of the instant disclosure, the exogenous nucleic acid encodes a chimeric antigen receptor (CAR). In some embodiments the exogenous nucleic acid encodes an epitope specific for a monoclonal antibody, a suicide polypeptide, an inducible "on" or "accelerator" switch or a control switch, e.g., a dimerization domain.

In some embodiments, the selected cell population is cultured in a vessel, wherein the vessel is a cell culture plate, cell culture deep well plate, a cell stack, a controlled bioreactor, a shake flask or a gas permeable bag. In some embodiments, the transduction culturing step comprises culturing the selected cell population and the retroviral vector in a volume of about 0.75 liters to a volume of about 250 liters of cell culture medium. In some embodiments, the transduction culturing step comprises culturing the selected cell population and the retroviral vector in a volume of about 0.5 liters to a volume of about 10 liters of cell culture medium.

In some embodiments, the retroviral vector used in the methods of instant disclosure is a lentiviral vector.

In some embodiments, at least 35% to 95%, 40% to 95%, 50% to 95%, 60% to 95%, 70% to 95%, of the transduced cell population expresses the exogenous nucleic acid gene product 3 to 18 days after initiation of the transduction culturing step. In some embodiments, at least 35% to 95%, 40% to 95%, 50% to 95%, 60% to 95%, 70% to 95%, of the transduced cell population expresses the exogenous nucleic acid gene product 7 to 18 days after initiation of the transduction culturing step.

In some embodiments, the cell culture media optionally comprises a co-localization agent during the transduction culturing step, such as fibronectin, fibronectin derivatives, polybrene or RetroNectin® reagent, during the transduction culturing step.

In some embodiments, the cell culture media does not comprise a co-localization agent, such as fibronectin or a fibronectin derivative, e.g., RetroNectin® reagent, during the transduction culturing step.

In some embodiments, the cell culture media does not comprise a co-localization agent during the transduction culturing step.

In some embodiments, a polycation, such as polybrene, protamine sulfate or DEAE-dextran, is not added to the cell culture media prior to or during transduction.

In some embodiments, the selected cell population is an allogeneic cell population. In some embodiments, the selected cell population is an autologous cell population.

In one aspect, a method for transducing a first and a second cell population, wherein the first and second cell population are transduced by the same method of the instant disclosure and whereby the percent of the transduced cell population expressing the exogenous nucleic acid gene product in the first and second transduced cell population does not vary more than 2% to 5%, 5% to 10%, 10% to 20%, or 20% to 30%, is provided.

In some embodiments, the methods of the instant disclosure provide a transduced cell population wherein a cell of the transduced cell population comprises a vector copy number which is reduced compared to a cell transduced by the same method of the instant disclosure wherein the starting pH of the transduction culturing step of the same method is less than 7.0.

In an aspect of the instant disclosure, a method for transducing a population of cytotoxic T cells with a retroviral vector, the vector comprising a nucleic acid exogenous to the cytotoxic T cells, the method comprising culturing the cytotoxic T cell population with the retroviral vector, in a cell culture media at starting pH in a starting pH range of 7.0 to 7.9 and maintaining the starting pH in the starting pH range for at least the first hour of the transduction culturing step to result in a transduced cytotoxic T cell population comprising cells expressing the gene product encoded by the exogenous nucleic acid and wherein the cell culture media does not comprise a co-localization agent, is provided.

In some embodiments of this aspect of the instant disclosure, the starting pH is maintained in a starting pH range of 7.0 to 7.9 for at least 1, 2, 4, 6, 8, 10, 12, 14, 16, 18, 20, 22 or 24 hours. In some embodiments, the starting pH of the cytotoxic T cell culture media is maintained in the starting pH range for at least about 1, about 2, about 4, about 6, about 8, about 10, about 12, about 14, about 16, about 18, about 20, about 22, about 24, about 36, about 48, about 72 or about 96 hours to no more than about 168 hours.

In some embodiments of this aspect, the starting pH of the cytotoxic T cell culture media is maintained in the starting pH range through the end of the transduction culturing step. In some embodiments, the transduction culturing step is conducted for at least 1, 2, 4, 6, 8, 12, 14, 16, 18, 20, 22, 24, 36, 48, 72 or 96 hours.

In some embodiments of this aspect of the instant disclosure the pH is controlled passively. In some embodiments, the pH is controlled actively.

In some embodiments, the cytotoxic T cell culture media does not comprise a co-localization agent, such as fibronectin or a fibronectin derivative, e.g., RetroNectin® during the transduction culturing step.

In some embodiments, a polycation, such as polybrene, protamine sulfate or DEAE-dextran, is not added to the cytotoxic T cell culture media prior to or during transduction.

In some embodiments of this aspect of the instant disclosure, the cytotoxic T cell population is cultured at a MOI of about 0.25, about 0.5, about 1, about 5, about 10, about 15, about 20, about 25, about 30, about 35, about 40, about 45, about, or about 50 to about 55, about 60, about 65, about 70, about 75, about 80, about 85, about 90, about 95, about 100, about 125, about 150, about 175, about 200, about 225, or about 250. In some embodiments the MOI is a ratio of functional viral particles to total number of cytotoxic T cells in a transduction procedure.

In some embodiments of this aspect of the instant disclosure, the exogenous nucleic acid encodes a chimeric antigen receptor. In some embodiments the exogenous nucleic acid encodes an epitope specific for a monoclonal antibody, a suicide polypeptide, an inducible "on" or "accelerator" switch or a control switch, e.g., a dimerization domain.

In some embodiments of this aspect of the instant disclosure, the cytotoxic T cell population is cultured in a vessel, wherein the vessel is a cell culture plate, cell culture deep well plate, a cell stack, a controlled bioreactor, a shake flask or a gas permeable bag. In some embodiments, the transduction culturing step comprises culturing the cytotoxic T cell population and the retroviral vector in a volume of about 0.75 liters to a volume of about 250 liters of cell culture media.

In some embodiments, the retroviral vector for use in the methods of instant disclosure is a lentiviral vector.

In some embodiments of this aspect of the instant disclosure, at least 40% to 95%, 50% to 95%, 60% to 95%, 70% to 95%, of the transduced cytotoxic T cell population expresses the exogenous nucleic acid gene product 3 to 18 days after initiation of the transduction culturing step. In some embodiments, at least 40% to 95%, 50% to 95%, 60% to 95%, 70% to 95%, of the transduced cytotoxic T cell population expresses the exogenous nucleic acid gene product 7 to 18 days after initiation of the transduction culturing step.

In some embodiments, the cytotoxic T cell population to be transduced is an allogeneic cytotoxic T cell population. In some embodiments, the cytotoxic T cell population to be transduced is an autologous cytotoxic T cell population.

In an aspect of the instant disclosure, a method for transducing a first and a second cytotoxic T cell population, wherein the first and second cytotoxic T cell population are transduced by the same method of the instant disclosure whereby the percent of the transduced cytotoxic T cell population expressing the exogenous nucleic acid gene product in the first and second transduced cytotoxic T cell population does not vary more than 2% to 5%, 5% to 10%, 10% to 20%, or 20% to 30%, is provided.

In an aspect of the instant disclosure, a method for transducing a population of peripheral blood mononuclear cells with a retroviral vector, the vector comprising a nucleic acid exogenous to the peripheral blood mononuclear cells, the method comprising culturing the peripheral blood mononuclear cell population with the retroviral vector, in a cell culture media at starting pH in a starting pH range of 7.0 to 7.9 and maintaining the starting pH in the starting pH range for at least the first hour of the transduction culturing step to result in a transduced peripheral blood mononuclear cell population comprising cells expressing the gene product encoded by the exogenous nucleic acid and wherein the cell culture media does not comprise a co-localization agent, is provided.

In some embodiments of this aspect of the instant disclosure, the starting pH is maintained in a starting pH range of 7.0 to 7.9 for at least 1, 2, 4, 6, 8, 10, 12, 14, 16, 18, 20, 22 or 24 hours. In some embodiments, the starting pH is maintained in the starting pH range for at least about 1, about 2, about 4, about 6, about 8, about 10, about 12, about 14, about 16, about 18, about 20, about 22, about 24, about 36, about 48, about 72 or about 96 hours to no more than about 168 hours.

In some embodiments of this aspect, the starting pH is maintained in the starting pH range through the end of the transduction culturing step. In some embodiments, the transduction culturing step is conducted for at least 1, 2, 4, 6, 8, 12, 14, 16, 18, 20, 22, 24, 36, 48, 72 or 96 hours.

In some embodiments of the instant disclosure the pH is controlled passively. In some embodiments, the pH is controlled actively.

In some embodiments, the peripheral blood mononuclear cell culture media does not comprise a co-localization agent, such as fibronectin or a fibronectin derivative, e.g., RetroNectin® during the transduction culturing step.

In some embodiments, a polycation, such as polybrene, protamine sulfate or DEAE-dextran, is not added to the peripheral blood mononuclear cell culture media prior to or during transduction.

In some embodiments of this aspect of the instant disclosure, the peripheral blood mononuclear cell population is cultured at a MOI of about 0.25, about 0.5, about 1, about 5, about 10, about 15, about 20, about 25, about 30, about 35, about 40, about 45, about, or about 50 to about 55, about 60, about 65, about 70, about 75, about 80, about 85, about 90, about 95, about 100, about 125, about 150, about 175, about 200, about 225, or about 250. In some embodiments the MOI is a ratio of functional viral particles to total number of peripheral blood mononuclear cells in a transduction procedure.

In some embodiments of this aspect of the instant disclosure, the exogenous nucleic acid encodes a chimeric antigen receptor. In some embodiments the exogenous nucleic acid encodes an epitope specific for a monoclonal antibody, a suicide polypeptide, an inducible "on" or "accelerator" switch or a control switch, e.g., a dimerization domain.

In some embodiments of this aspect of the instant disclosure, the peripheral blood mononuclear cell population is cultured in a vessel, wherein the vessel is a cell culture plate, cell culture deep well plate, a cell stack, a controlled bioreactor, a shake flask or a gas permeable bag. In some embodiments, the transduction culturing step comprises culturing the peripheral blood mononuclear cell population and the retroviral vector in a volume of about 0.75 liters to a volume of about 250 liters of cell culture media.

In some embodiments, the retroviral vector for use in the methods of this aspect of the instant disclosure is a lentiviral vector.

In some embodiments of this aspect of the instant disclosure, at least 40% to 95%, 50% to 95%, 60% to 95%, 70% to 95%, of the transduced peripheral blood mononuclear cell population expresses the exogenous nucleic acid gene product 3 to 18 days after initiation of the transduction culturing step. In some embodiments, at least 40% to 95%, 50% to 95%, 60% to 95%, 70% to 95%, of the transduced peripheral blood mononuclear cell population expresses the exogenous nucleic acid gene product 7 to 18 days after initiation of the transduction culturing step.

In some embodiments, the peripheral blood mononuclear cell population to be transduced is an allogeneic peripheral blood mononuclear cell population. In some embodiments, the peripheral blood mononuclear cell population to be transduced is an autologous peripheral blood mononuclear cell population.

In an aspect of the instant disclosure, a method for transducing a first and a second peripheral blood mononuclear cell population, wherein the first and second peripheral blood mononuclear cell population are transduced by the same method of the instant disclosure whereby the percent of the transduced peripheral blood mononuclear cell population expressing the exogenous nucleic acid gene product in the first and second transduced peripheral blood mononuclear cell populations does not vary more than 2% to 5%, 5% to 10%, 10% to 20%, or 20% to 30%, is provided.

In an aspect of the instant disclosure, a method for transducing a population of T cells derived from induced pluripotent stem cells with a retroviral vector, the vector comprising a nucleic acid exogenous to the derived T cells, the method comprising culturing the derived T cell population with the retroviral vector, in a cell culture media at starting pH in a starting pH range of 7.0 to 7.9 and maintaining the starting pH in the starting pH range for at least the first hour of the transduction culturing step to result in a transduced derived T cell population comprising cells expressing the gene product encoded by the exogenous nucleic acid and wherein the cell culture media does not comprise a co-localization agent, is provided.

In some embodiments of this aspect of instant disclosure, the starting pH is maintained in a starting pH range of 7.0 to 7.9 for at least 1, 2, 4, 6, 8, 10, 12, 16, 18, 20, 22 or 24 hours. In some embodiments, the starting pH of the culture media for the T cell population derived from induced pluripotent stem cells is maintained in the starting pH range for at least about 1, about 2, about 4, about 6, about 8, about 10, about 12, about 14, about 16, about 18, about 20, about 22, about 24, about 36, about 48, about 72 or about 96 hours to no more than about 168 hours.

In some embodiments of this aspect, the starting pH of the derived T-cell culture media is maintained in the starting pH range through the end of the transduction culturing step. In some embodiments, the transduction culturing step is conducted for at least 1, 2, 4, 6, 8, 12, 14, 16, 18, 20, 22, 24, 36, 48, 72 or 96 hours.

In some embodiments of this aspect of the instant disclosure the pH of the derived T-cell culture media is controlled passively. In some embodiments, the pH is controlled actively.

In some embodiments of this aspect of the invention, the derived T-cell culture media does not comprise a co-localization agent, such as fibronectin or a fibronectin derivative, e.g., RetroNectin® during the transduction culturing step.

In some embodiments, a polycation, such as polybrene, protamine sulfate or DEAE-dextran, is not added to the derived T-cell culture media prior to or during transduction.

In some embodiments of this aspect of the instant disclosure, the derived T cell population is cultured at a MOI of about 0.25, about 0.5, about 1, about 5, about 10, about 15, about 20, about 25, about 30, about 35, about 40, about 45, about, or about 50 to about 55, about 60, about 65, about 70, about 75, about 80, about 85, about 90, about 95, about 100, about 125, about 150, about 175, about 200, about 225, or about 250. In some embodiments the MOI is a ratio of functional viral particles to the total number of T cells derived from induced pluripotent stem cells in a transduction procedure.

In some embodiments of this aspect of the instant disclosure, the exogenous nucleic acid encodes a chimeric antigen receptor. In some embodiments the exogenous nucleic acid encodes an epitope specific for a monoclonal antibody, a suicide polypeptide, an inducible "on" or "accelerator" switch or a control switch, e.g., a dimerization domain.

In some embodiments of this aspect of the instant disclosure, the derived T cell population is cultured in a vessel, wherein the vessel is a cell culture plate, cell culture deep well plate, a cell stack, a controlled bioreactor, a shake flask or a gas permeable bag. In some embodiments, the transduction culturing step comprises culturing the derived T cell population and the retroviral vector in a volume of about 0.5 liters to a volume of about 10 liters of cell culture media.

In some embodiments, the retroviral vector for use in the methods of instant disclosure is a lentiviral vector.

In some embodiments of this aspect of the instant disclosure, 35% to about 95%, about 40% to about 95%, about 50% to about 95%, about 60% to about 95%, or about 70% to about 95%, of the transduced derived T cell population expresses the exogenous nucleic acid gene product 3 to 18 days after initiation of the transduction culturing step. In some embodiments, about 35% to about 95%, about 40% to about 95%, about 50% to about 95%, about 60% to about 95%, or about 70% to about 95%, of the transduced derived T cell population expresses the exogenous nucleic acid gene product 7 to 18 days after initiation of the transduction culturing step.

In some embodiments, the derived T cell population to be transduced is an allogeneic derived T cell population. In some embodiments, the derived T cell population to be transduced is an autologous derived T cell population.

In an aspect of the instant disclosure, a method for transducing a first and a second derived T cell population, wherein the first and second derived T cell population are transduced by the same method of the instant disclosure whereby the percent of the transduced derived T cell population expressing the exogenous nucleic acid gene product in the first and second transduced derived T cell population does not vary more than 2% to 5%, 5% to 10%, 10% to 20%, or 20% to 30%, is provided.

In some embodiments of the present invention, a genetically modified cell produced by the methods of instant disclosure is provided. In another embodiment of the present invention, a population of genetically modified cells produced by the methods of instant disclosure is provided. In another embodiment, a therapeutic composition comprising a cell or cell population produced by the methods of the invention is provided. In another embodiment, a method of treatment comprising administering a therapeutic effective amount of a cell, cell population or therapeutic composition produced by the methods of the instant invention to a subject in need thereof is provided.

BRIEF DESCRIPTION OF THE DRAWINGS

FIGS. 2A and 2B show that the averaged percentage of viable CAR+ T cells, on Day 11 of the study, when the cells are transduced at pH of 7.1 (FIG. 2A) is 81.28587 or 23.0387 when transduced at pH 6.6 (FIG. 2B), as determined by ANOVA analysis.

FIG. 2C shows the p-values for the main effects and 2-way interactions of pH, % lentivirus vector (v/v) (indicated as LVV), RetroNectin® reagent concentration (μg/mL) (indicated as RN), and vessel type on the percentage of viable CAR+ T cells.

DETAILED DESCRIPTION

Figure 1:
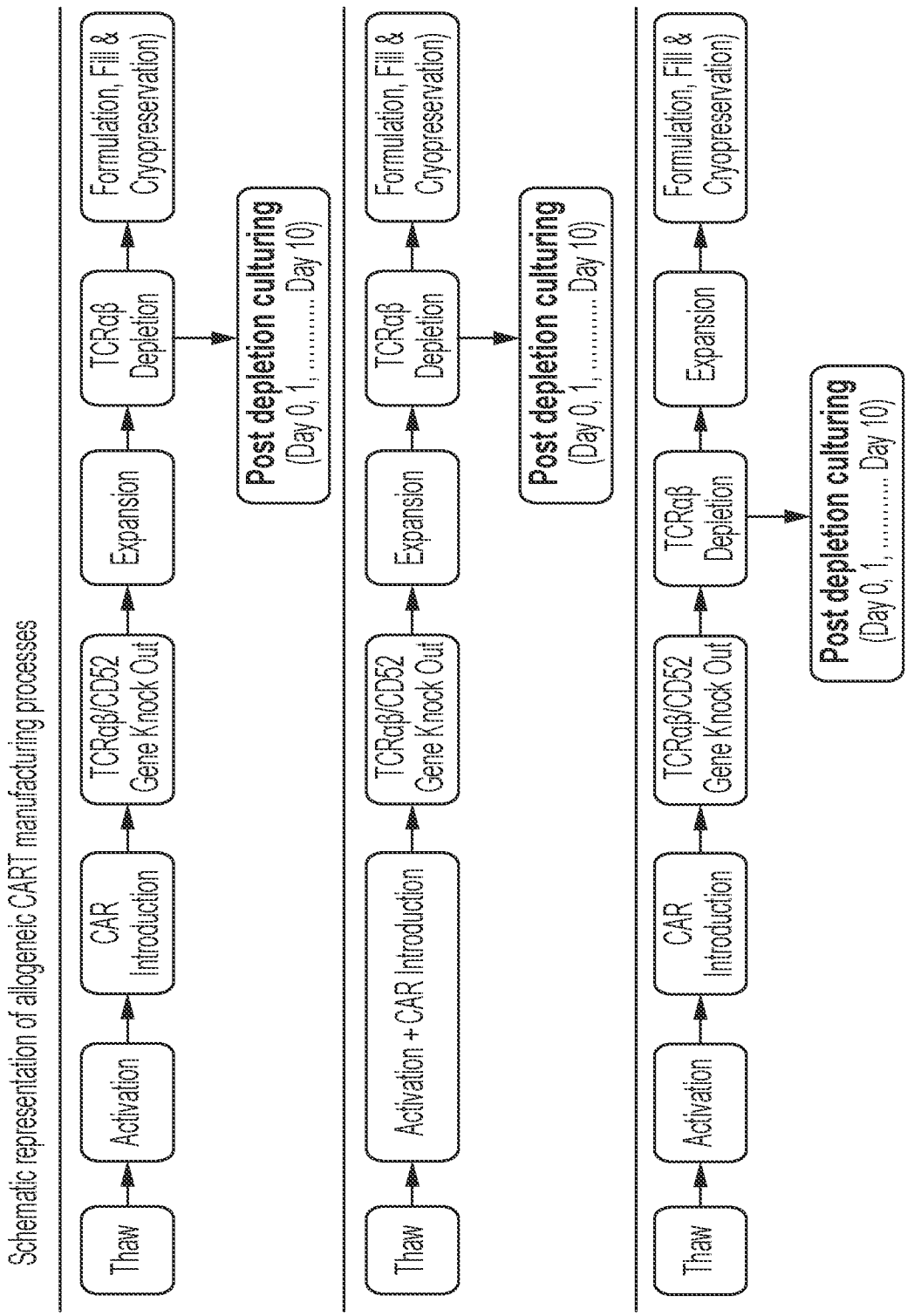
FIG. 1 shows exemplary protocols for isolating PBMCs, activating, transducing, transfecting, expanding, and harvesting T cells from the isolated PBMCs.
Figure 1:
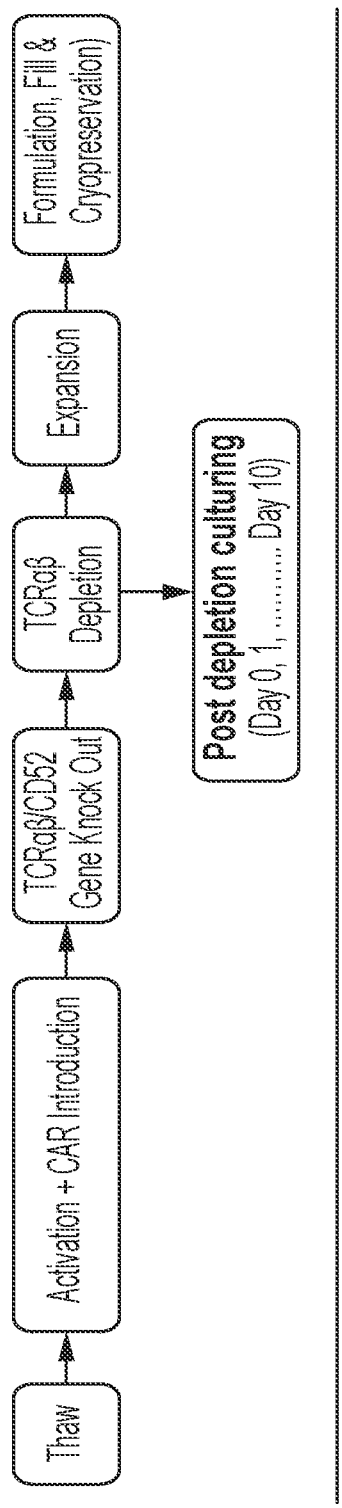

Provided herein, are improved methods for transducing immune cells, particularly T-cells, that increase transduction efficiency and/or improve the consistency of exogenous nucleic acid expression levels between production runs while reducing processing costs and complexity.

Illustrative methods provided herein, which are typically ex vivo methods, include transducing activated T-cells with retrovirus vectors or retroviral vectors to produce genetically modified T-Cells. In illustrative embodiments, the transducing step can be conducted without a co-localization agent. In further illustrative embodiments, the transducing step can be conducted at a pH of 6.9 to 7.8, or a pH of 7.0 to 7.9. Typically, such methods can include enriching peripheral blood mononuclear cells (PBMCs) to isolate PBMCs that comprise T-cells that can be used in the activating step. Further, in illustrative embodiments, such methods can include expanding genetically modified T-cells. In further illustrative embodiments, the methods provided herein can further comprise disrupting an endogenous gene in the T-cells. In illustrative embodiments of the methods provided herein, T-cells can be activated, transduced and typically expanded. Such T-cells in the illustrative embodiments can be genetically modified to express a CAR.

Definitions

While the terminology used in the instant disclosure is standard within the art, definitions of certain terms are provided herein to assure clarity and definiteness to the meaning of the claims. Units, prefixes, and symbols can be denoted in their SI accepted form. As described herein, any concentration range, percentage range, ratio range or integer range is to be understood to include the value of any integer within the recited range and, when appropriate, fractions thereof (such as one-tenth and one-hundredth of an integer), unless otherwise indicated. The section headings used herein are for organizational purposes only and are not to be construed as limiting the subject matter described.

As used in the instant disclosure, except as otherwise expressly provided herein, each of the following terms shall have the meaning set forth below. Additional definitions are set forth throughout the disclosure.

Unless otherwise noted, the terms "a" or "an" are to be construed as meaning "at least one or more of".

The term "about" as used in connection with a numerical value throughout the specification and the claims denotes an interval of accuracy, familiar and acceptable to a person skilled in the art. In general, such interval of accuracy is plus or minus 0.15%.

The term "activation" or "activated" refers to the state of an immune cell, e.g., a T cell, that has been sufficiently stimulated to induce detectable cellular proliferation. Activation can also be associated with induced cytokine production and detectable effector functions. The term "activated T cells" refers to, among other things, T cells that are undergoing cell division. T cell activation can be characterized by increased T cell expression of one or more biomarker, including, but not limited to, CD57, PD1, CD107a, CD25, CD137, CD69, and/or CD71.

The term "administering" refers to the physical introduction of an agent to a subject, using any of the various methods and delivery systems known to those skilled in the art. Exemplary routes of administration for the T cells prepared by the methods disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular subcapsular, subarachnoid, intraspinal, epidural and intrasternal injection and infusion, as well as in vivo electroporation. Administering can also be performed, for example, once, a plurality of times, and/or over one or more extended periods.

The term "allogeneic" refers to any material derived from one individual which is then introduced to another individual of the same species, e.g., allogeneic T cell transplantation or therapy.

The term "antibody" (Ab) includes, without limitation, an immunoglobulin which binds specifically to an antigen. In general, an antibody can comprise at least two heavy (H) chains and two light (L) chains interconnected by disulfide bonds. Each H chain comprises a heavy chain variable region (abbreviated herein as VH) and a heavy chain constant region. The heavy chain constant region can comprise three or four constant domains, CH1, CH2 CH3, and/or CH4. Each light chain comprises a light chain variable region (abbreviated herein as VL) and a light chain constant region. The light chain constant region can comprise one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The term "antibody" includes, by way of example, both naturally occurring and non-naturally occurring Abs; monoclonal and polyclonal Abs; bispecific antibodies; minibodies; domain antibodies; chimeric and humanized Abs; human or nonhuman Abs; wholly synthetic Abs (sometimes referred to "antibody mimetics"); camelid antibodies; antibody fusions (sometimes referred to as "antibody conjugates") and single chain Abs. A nonhuman Ab can be humanized by recombinant methods to reduce its immunogenicity in man.

An "immunoglobulin" as used herein can derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes.

The term "autologous" refers to any material derived from the same individual to which it is later to be re-introduced. For example, engineered autologous cell therapy (eACT™) involves collection of lymphocytes from a donor, e.g., a patient, which are then engineered to express, e.g., a CAR construct, and then administered back to the same donor e.g., a patient.

The term "co-localization agent" as used herein refers to a reagent that promotes the co-localization of a viral vector or particle, e.g., a retroviral or lentiviral particle with target cells, e.g., immune cells such as T-cells, and can include, for example, fibronectin or fibronectin derivatives, such as the RetroNectin® reagent.

The term "manufacturing scale transduction volume" as used herein refers to a volume of 500 mLs up to 5 liters.

The term "multiplicity of infection" (hereinafter "MOI") refers to the ratio of infectious agents, such as virus particles, to infection targets, e.g., cells, in the media of a procedure, such as a transduction procedure. In some embodiments, MOI may be equal to the number of functional viral particles added to the total number of target cells during a transduction procedure. In some embodiments, the number of functional viral particles added to a transduction procedure is determined by ascertaining the titer of the functional viral particles. In some embodiments, the titer of functional viral particles is determined by using qPCR to determine the number of nucleic acid viral copies integrated per cell in as stably transduced standard cell line using techniques known in the art. See, e.g., Paugh, B. S., et al. *Sci Rep* 11, 389 (2021) herein incorporated by reference in its entirety. In some embodiments, the viral particles are retroviral particles. In some embodiments, the viral particles are lentiviral particles.

As used herein pH control can be active, for example where cell culture pH is continuously controlled in a bioreactor with pH feedback control or passive, for example where the cell culture pH is controlled at the culture initiation by adjusting the buffered cell culture media and % $CO_2$ in the tissue culture incubator to achieve the predetermined pH and not controlled further.

The terms "selective" or "specific" and associated derivatives are used interchangeably herein. A molecule, such as an antigen binding domain, is said to be selective or specific when it binds to one target more tightly than it binds to a second target.

The term vector copy number ("VCN") as used herein refers to the number of vector copies, e.g., viral vector copies, per cell.

The terms "viral vector" and "retroviral vector" as used interchangeably herein denote any form of a nucleic acid derived from a retrovirus and used to transfer genetic material into a cell via transduction. The term encompasses viral vector nucleic acids, such as DNA and RNA, encapsulated forms of these nucleic acids, and viral particles in which the viral vector nucleic acids have been packaged.

Immune Cells

Prior to the in vitro manipulation or genetic modification of the immune cells described herein, the cells can be obtained from a subject. The immune cells can be obtained from an allogenic or autologous source subject (i.e., from a healthy donor or a patient).

Immune cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In some embodiments, any number of T-cell lines available and known to those skilled in the art, can be used. In some embodiments, cells can be derived from a healthy donor, from a patient diagnosed with cancer or from a patient diagnosed with an infection. In some embodiments, cells can be part of a mixed population of cells which present different phenotypic characteristics.

In some embodiments, the immune cells comprise T cells. T cells can be obtained from a number of sources, including peripheral blood mononuclear cells (PBMCs), bone marrow, lymph nodes tissue, cord blood, thymus tissue, tissue from a site of infection, ascites, pleural effusion, spleen tissue, and tumors. In certain embodiments, T-cells can be obtained from blood collected from a subject using any number of techniques known to the skilled person, such as FICOLL™ separation.

In some embodiments, the immune cells can be derived from stem cells, such as a progenitor cell, a bone marrow stem cell, an inducible pluripotent stem cell, an iPSC, hematopoietic stem cell, and a mesenchymal stem cell. iPS cells and other types of stem cells can be cultivated immortal cell lines or isolated directly from a patient. In some embodiments, the immune cells are T-cells derived from induced pluripotent stem cells. Various methods for isolating, developing, and/or cultivating stem cells are known in the art and can be used to practice the present the instant disclosure.

In some embodiments, the immune cell is an induced pluripotent stem cell (iPSC) derived from a reprogrammed T-cell. In some embodiments, the source material can be an induced pluripotent stem cell (iPSC) derived from a T cell or non-T cell. The source material can alternatively be a B cell, or any other cell from peripheral blood mononuclear cell isolates, hematopoietic progenitor, hematopoietic stem cell, mesenchymal stem cell, adipose stem cell, or any other somatic cell type.

Blood Collection

In some embodiments the T-cells to be engineered are obtained from PBMCs. In some embodiments, the PBMCs can be collected or obtained from a subject by any suitable method known in the art. For example, in some embodiments, the blood can be collected by venipuncture or any other blood collection method by which a sample of blood and/or PBMCs is collected.

In some embodiments, PBMCs can be obtained from the circulating blood of an individual by apheresis. The apheresis product typically contains lymphocytes, including T cells, monocytes, granulocytes, B cells, other nucleated white blood cells, red blood cells, and platelets. In certain embodiments, the cells collected by apheresis, particularly leukopheresis, can be washed to remove the plasma fraction, and placed in an appropriate buffer or media for subsequent processing.

T Cell Enrichment

In certain embodiments, T cells are isolated from PBMCs by lysing the red blood cells and depleting the monocytes, for example, using centrifugation through a PERCOLL™ gradient. A specific subpopulation of T-cells, (e.g., CD28+, CD4+, CDS+, CD45RA−, CD45RO+, CDS+, CD62−, CD95−, CD95+, TL2R+, IL2R−, CCR7+, CCR7−, CDL−, CD62L+ and combinations thereof) can be further isolated by positive or negative selection techniques known in the art. In one example the subpopulation of T-cells is CD45RA+, CD95−, IL-2R−, CCR7+, CD62L+. In one example the subpopulation of T-cells is CD45RA+, CD95+, IL-2R+, CCR7+, CD62L+. In one example the subpopulation of T-cells is CD45RO+, CD95+, IL-2R+, CCR7+, CD62L+. In one example the subpopulation of T-cells is CD45RO+, CD95+, IL-2R+, CCR7−, CD62L−. In one example the subpopulation of T-cells is CD45RA+, CD95+, IL-2R+, CCR7−, CD62L−. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CDI lb, CD16, HLA DR, and CD8. Flow cytometry and cell sorting can also be used to isolate cell populations of interest for use in the methods and embodiments of the present disclosure.

PBMCs can be used directly for genetic modification, e.g., introduction of a CAR, using methods as described herein. It will be appreciated that PBMCs can further include other cytotoxic lymphocytes such as NK cells or NKT cells. An expression vector carrying the coding sequence of a chimeric antigen receptor as disclosed herein can be introduced into a population of human donor T cells, NK cells or NKT cells. Successfully transduced T cells that carry the expression vector can be sorted using flow cytometry to isolate CD3 positive T cells and then further propagated to increase the number of these CAR expressing T cells in addition to cell activation using anti-CD3 antibodies and IL-2 or other methods known in the art as described elsewhere herein.

In certain embodiments, after isolating the PBMCs, T lymphocytes can be further isolated and both cytotoxic and helper T lymphocytes can be sorted into naive, memory, and effector T cell subpopulations either before or after genetic modification and/or expansion.

In some embodiments, CD8+ cells are further sorted into naive, stem cell memory, central memory, and effector cells by identifying characteristic cell surface antigens that are associated with each of these types of CD8+ cells. In some embodiments, the expression of phenotypic markers of central memory T cells include CD45RO, CD62L, CCR 7, CD28, CD3, and CD127 and are negative for granzyme B. In some embodiments, stem cell memory T cells are CD45RO−, CD62L+, CD8+ T cells. In some embodiments, central memory T cells are CD45RO+, CD62L+, CD8+ T cells. In some embodiments, effector T cells are negative for CD62L, CCR 7, CD28, and CD127, and positive for granzyme B and perforin.

In certain embodiments, CD4+ T cells are further sorted into subpopulations. For example, CD4+T helper cells can be sorted into naive, central memory, and effector cells by identifying cell populations that have characteristic cell surface antigens.

Cell Activation and Expansion

The immune cells of the disclosure can be activated and expanded, either prior to or after genetic modification of the immune cells. FIG. 1 shows exemplary protocols that can be used for activating, transducing, transfecting and expanding immune cells of the instant disclosure. In one embodiment, the in vitro transduction, transfection, culture and/or expansion of T cells are performed in the absence of non-human animal derived products such as fetal calf serum and fetal bovine serum.

Generally, the engineered immune cells of the disclosure can be expanded, for example, by contacting with an agent that stimulates a CD3 TCR complex and a costimulatory molecule on the surface of the T cells to create an activation signal for the T cell. For example, chemicals such as calcium ionophore A23187, phorbol 12-myristate 13-acetate (PMA), or mitogenic lectins like phytohemagglutinin (PHA) can be used to create an activation signal for the T cell.

In some embodiments, T cell populations can be stimulated in vitro by contact with, for example, an anti-CD3 antibody such as OKT3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T-cells can be contacted with an anti-CD3 antibody (e.g., an OKT3 antibody) and an anti-CD28 antibody, under conditions appropriate for stimulating proliferation of the T cells. The anti-CD3 antibody and an anti-CD28 antibody can be disposed on a bead, such as a plastic or magnetic bead, or plate or other substrate. Conditions appropriate for T cell culture include an appropriate media (e.g., Minimal Essential Media or RPMI Media 1640 or, X-vivo 15, (Lonza)) that can contain factors necessary for proliferation and viability, including serum (e.g., fetal bovine or human serum), interleukin-2 (IL-2), insulin, IFN-γ, IL-4, IL-7, GM-CSF, IL-10, IL-2, IL-15, TGFb, and TNF, or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, AlM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells (e.g., IL-7 and/or IL-15). Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times can exhibit different characteristics. In some embodiments, the cells of the disclosure can be expanded by co-culturing with tissue or cells. The cells can also be expanded in vivo, for example in the subject's blood after administering the cell into the subject.

Conditions appropriate for T cell culture include an appropriate media (e.g., Minimal Essential Media or RPMI Media 1640 or, X-vivo 15, (Lonza)) that can contain factors necessary for proliferation and viability, including serum (e.g., fetal bovine or human serum), interleukin-2 (IL-2), insulin, IFN-γ, IL-4, IL-7, GM-CSF, IL-10, IL-2, IL-15, TGFb, and TNF, or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells (e.g., IL-7 and/or IL-15). Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times can exhibit different characteristics. In some embodiments, the cells of the disclosure can be expanded by co-culturing with tissue or cells. The cells can also be expanded in vivo, for example in the subject's blood after administering the cell into the subject.

Methods for activating and expanding T cells are known in the art and are described, for example, in U.S. Pat. Nos. 6,905,874; 6,867,041; 6,797,514; and WO2012/079000, the contents of which are hereby incorporated by reference in their entirety. Generally, such methods include contacting PBMC or isolated T cells with a stimulatory molecule and a costimulatory molecule, such as anti-CD3 and anti-CD28 antibodies, generally attached to a plastic or magnetic bead or other surface, in a culture medium with appropriate cytokines, such as IL-2. Anti-CD3 and anti-CD28 antibodies attached to the same bead serve as a "surrogate" antigen presenting cell (APC). One example is the Dynabeads® system, which is a CD3/CD28 activator/stimulator system for physiological activation of human T cells. In other embodiments, the T cells can be activated and stimulated to proliferate with feeder cells and appropriate antibodies and cytokines using methods such as those described in U.S. Pat. Nos. 6,040,177; 5,827,642; and WO2012129514, the contents of which are hereby incorporated by reference in their entirety. In another embodiment, the cells are activated and expanded with an anti-CD3/28 nanometer scale matrix that comprises antibodies and/or fragments thereof that bind CD3 and CD 28 as provided by Miltenyi Biotec Inc (Auburn, California) as TransAct™ T Cell Reagent (see e.g., catalog number 200-076-202 MACS GMP T Cell Transact-CRR, catalog number 130-019-011 MACS GMP T Cell Transact for Research use).

Transduction

Methods are provided herein, for genetically modifying immune cells, including PBMCs and T cells that are produced by the methods of the instant disclosure. In some embodiments of the methods and compositions disclosed herein, T cells are contacted ex vivo with replication incompetent retroviral vectors to genetically modify the T cells to express an exogenous gene product. In some embodiments, the exogenous gene product is a CAR.

In some embodiments the exogenous gene product is an epitope specific for (i.e., specifically recognized by) a monoclonal antibody, a suicide polypeptide, an inducible "on" or "accelerator" switch, such as inducible caspase-9 (U.S. Appl. 2011/0286980) or a thymidine kinase or an "off" switch. Exemplary mAb-specific epitopes are disclosed in International Patent Publication No. WO 2016/120216, which is incorporated herein in its entirety. In some embodiments, the exogenous gene product is an R epitope such as RQR8. See, e.g., WO2013153391A, which is hereby incorporated by reference in its entirety. Rituximab can bind R epitopes, when expressed on the surface of a CAR immune cell, causing the CAR immune cell to lyse. In some embodiments, the exogenous gene product is a control switch such as dimerization domain.

In some embodiments, transduction can be performed in the same vessel in which the activating step is performed without removing any of the media. For example, blood cells, such as PBMCs enriched and isolated from the collected blood sample, can be activated in a gas permeable bag and then contacted with retroviral particle in the same gas permeable bag. In illustrative embodiments, blood cells are separated, isolated, and/or purified away from granulocytes, including neutrophils prior to contacting with the retroviral vectors. The retroviral vectors, which in further illustrative embodiments can be replication incompetent recombinant lentiviral particles, can be introduced into the same gas permeable bag that contains the activated PBMCs, to form a transduction reaction mixture. In some embodiments, the retroviral vector is added to the transduction reaction mixture during the activating step. In some embodiments, the retroviral vector is added to the transduction reaction mixture after the activation step. In some embodiments, the activation step whether prior or simultaneous with the transduction step is carried out for no more than 12, 24, 36, 48, 60, 72, 84, 96, 108, 120, 132, 144, or 156 hours. FIG. 1 illustrates potential transduction timepoints in exemplary CAR T cell production protocols. Media is typically present during the transduction, such as those known in the art for culturing of T cells ex vivo, including base media and supplements including cytokines such as disclosed in further detail herein, see, e.g., Activation and Expansion description above.

The transduction reaction, which in some embodiments begins when the retroviral vectors are added to the T cells, can be incubated at between 23 and 39° C., and in some illustrative embodiments at 37° C. In some embodiments, the transduction reaction can be carried out at 37-39° C. In some embodiments the transduction reaction is incubated at 0.5, 1.0, 2.0, 3.0, 4.0, 5.0, 6.0, 7.0, 8.0, 9.0 and 10.0% $CO_2$. The transduction reaction can be incubated for at least 1, 2, 3, 4, 5, 6, 7, 8, 9, 10, 11, 12, 13, 14, 15, 16, 17, 18, 19, 20, 24, 25, 24, 36, 48, up to 1, 2, 3, 4, 5, 6, 7, 8, 9, 10, 11 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 72 or 96 hours. In illustrative embodiments, the transduction reaction can be incubated for between 1 to 2, 1 to 3, 1 to 4, 1 to 5, 1 to 6, 1 to 7, 1 to 8, 1 to 9, 1 to 10, 4 to 12, 4 to 14, 4 to 16, 4 to 18, 4 to 20, 4 to 24, 4 to 26, 4 to 28, 4 to 30, 4 to 32, 4 to 36, 4 to 38, 4 to 40, 4 to 42, 4 to 44, 4 to 46, 4 to 48, or 4 to 72 hours at a pH in the starting pH range. In some embodiments, the transduction reaction pH is controlled passively, for example by adjusting media buffering (e.g., sodium bicarbonate and/or HEPES) and incubator pCO2 to allow desired pH (such as pH greater than 7.0) at culture initiation, to achieve a target pH, such as 7.0 or higher. In some embodiments, the transduction reaction pH is actively controlled, for example by using a bioreactor that has online pH measurement and with a pH feedback control loop that maintains pH by continuously (actively) modulating the culture pH via $CO_2$ gas addition.

In some embodiments, T cells can be transduced with different ratios of retroviral or lentiviral particles to cells, referred to as the multiplicity of infection (MOI). In some embodiments, the T cells are transduced using a MOI (plaque forming units/cell) between 0.25, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 50, 100, 150, 200, 250, 300, 350, 400, 450 to 500. In some embodiments, the T cells are transduced at a MOI between 0.25, 0.50, 1.0, 5, 10, 15, 20, 25, or 30 to 50, 75, 100, 125, 150, 175 or 200. In some embodiments, the T cells are transduced at an MOI of about 1 to 10, 15, 20, 25, 30, 35, 40, 45 or 50. In some embodiments, the T cells are transduced at an MOI of 1 to 20.

In some embodiments of the methods and compositions disclosed herein, between 25% and 90% of the T cells express the exogenous gene product, in some embodiments, between 25%, 30%, 35%, 40%, 45%, 50%, 55%, 60% 65%, 70%, 75%, 80%, or 85%, to 90% of the transduced T cells express the exogenous gene product.

In some embodiments, the percent of transduced T cells that express the exogenous gene product can be at least 30%, 35%, 40%, 45%, 50%, 55%, 60%, 65%, 70%, 75%, 80%, 85% or 90%, more particularly at least 40%, 45%, 50%, 55%, 60% 65%, 70%, 75%, or 80% and more particularly at least 60% 65%, 70%, 75% or 80%. In some embodiments, the indicated exogenous gene product expression levels are achieved on 1, 2, 3, 4, 5, 6, 7, 8, 9, 10, 11, 12, 13, 14, 15, 16, 17, 18, 19, or 20, particularly 3-10 days after the retroviral vectors are first contacted with the cells during the transduction reaction.

In some embodiments the transduction reaction occurs in a volume of 0.25 to 250, 0.25 to 7.5, 0.375 to 7.5, 0.5 to 5, or 0.7 to 4.0 liters transduction culture media. In some embodiments the transduction reaction occurs in a volume of at least 0.25, 0.50, 0.75, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 50, 100, 150, 200, or 250 liters of transduction culture medium. In some embodiments the transduction reaction occurs in a volume of at about 0.25, about 0.50, about 0.60, or about 0.75, to about 0.8, about 1.0, about 1.5, about 2.0, about 2.5, about 3.0, about 3.5, about 4.0, about 4.5, about 5.0, about 7.5, about 8.0, or about 10.0 liters of transduction culture medium.

In some embodiments, the cell is transduced by a viral vector comprising a nucleic acid exogenous to the cell. In some embodiments the exogenous nucleic acid encodes a CAR. In some embodiments the viral vector is a retrovirus, lentivirus or an AAV vector.

The cells to be transduced to express a CAR can be derived from an allogenic or autologous source. In one embodiment, the in vitro transduction, culture and/or expansion of T cells are performed in the absence of non-human animal derived products such as fetal calf serum and fetal bovine serum.

In some embodiments, the transduction reaction cell population is incubated from 1 hour to 2, 3, 4, 5, 6, 7, 8, 9, 10, 12, 24, or 48 hours, with a retroviral vector encoding a CAR at a MOI of at least 5, 10, 20, 30, 50, 100, 150, or 200, at a pH in the starting pH range and at or below 7.8 or at or below 7.9, and wherein at least 40%, 45%, 50%, 55%, 60%, 65%, 70%, 75%, 80%, or 85% of the T cells express the CAR by at least Day 3, 4, 5, 6, 7, 8, 9 or 10 after the retroviral vector was first contacted with the cells during the transduction reaction.

Gene Disruption

The process for manufacturing allogenic CAR T therapy or AlloCARs™ involves harvesting healthy, selected, screened and tested T cells from healthy donors. Allogeneic T cells are gene editing to reduce the risk of graft versus host disease (GvHD) and to prevent allogeneic rejection. In some embodiments a selected T cell receptor gene (e.g., TCRa or TCRb) is knocked out to avoid GvHD. The CD52 gene can also be knocked out to render the CART product resistant to anti-CD52 antibody treatment. Anti-CD52 antibody treatment can therefore be used to lymphodeplete the host immune system and allow the CART cells to stay engrafted to achieve full therapeutic impact. In one example, an anti-CD52 antibody can comprise alemtuzumab (CHEMBL 1201587, ChemIDplus:216503-57-0; DB00087; see also U.S. Pat. No. 5,846,534, both of which are incorporated herein in their entireties, for all purposes). Next, the T cells are engineered to express CARs, which recognize certain cell surface proteins that are expressed in hematologic or solid tumors. The engineered T cells then undergo a purification step and are ultimately cryopreserved in vials.

The process for manufacturing autologous chimeric antigen receptor (CAR) T cell therapy, involves collecting a patient's own cells (e.g., white blood cells, including T cells) and genetically engineering the T cells to express CARs that recognize a target antigen expressed on the cell surface, such as cancer cell antigen for example. The engineered cells are then cryopreserved and subsequently administered to the patient from which the cells were removed for engineering.

In some embodiments, the isolated immune cells are genetically modified to reduce or eliminate expression of endogenous TCRa and/or CD52. In some embodiments, the cells are genetically modified using gene editing technology (e.g., CRISPR/Cas9, CRISPR/CAS 12, a zinc finger nuclease (ZFN), a TALEN®, a MegaTAL, a meganuclease) to reduce or eliminate expression of endogenous proteins (e.g., TCRa and/or CD52) In some embodiments the method comprises disrupting or inactivating one or more genes by introducing into the cells an endonuclease able to inactivate a target gene by DNA cleavage. In some embodiments the endonuclease can be, for example, a zinc finger nuclease (ZFN), megaTAL nuclease, meganuclease, transcription activator-like effector nuclease (TALE-nuclease/TALEN), or CRISPR (e.g., Cas9, Cas12 or CAS14) endonuclease.

In some embodiments, the immune cell is transfected by a nucleic acid vector using electroporation, sonoporation, biolistics (e.g., Gene Gun), lipid transfection, polymer transfection, nanoparticles, or polyplexes. In some embodiments, the isolated immune cells are genetically modified to reduce or eliminate expression of endogenous TCRa and/or CD52.

Expansion and Depletion

In illustrative embodiments of the methods disclosed herein, transduced T cells can be expanded before harvesting as described generally in the Activation and Expansion description above. In some embodiments, transduced cells are further transfected to knock out a target endogenous gene. In some embodiments, the transduced cells are depleted of undesired cell types, for e.g., cells expressing TCRαβ. As indicated in FIG. 1, in some embodiments the transduced cells can be expanded prior to depletion or after depletion.

Flow cytometry can be used to deplete specific cell types, such as T cell receptor positive cells, within a population of cells. In general, flow cytometry is a method for quantitating components or structural features of cells primarily by optical means. Since different cell types can be distinguished by quantitating structural features, flow cytometry and cell sorting can be used to count and sort cells of different phenotypes in a mixture.

A flow cytometry analysis involves two primary steps: 1) labeling selected cell types with one or more labeled markers, and 2) determining the number of labeled cells relative to the total number of cells in the population. In some embodiments, the method of labeling cell types includes binding labeled antibodies to markers expressed by the specific cell type, such as a T-Cell receptor. The antibodies can be either directly labeled with a fluorescent compound or indirectly labeled using, for example, a fluorescent-labeled second antibody which recognizes the first antibody.

In some embodiments, the method used for sorting T cells expressing CAR is the Magnetic-Activated Cell Sorting (MACS). Magnetic-activated cell sorting (MACS) is a method for separation of various cell populations depending on their surface antigens (CD molecules) by using superparamagnetic nanoparticles and columns. MACS can be used to obtain a pure cell population.

Cells in a single-cell suspension can be magnetically labeled with microbeads. The sample is applied to a column composed of ferromagnetic spheres, which are covered with a cell-friendly coating allowing fast and gentle separation of cells. The unlabeled cells pass through while the magnetically labeled cells are retained within the column. The flow-through can be collected as the unlabeled cell fraction. After a washing step, the column is removed from the separator, and the magnetically labeled cells are eluted from the column.

Detailed protocols for the purification of specific cell population such as T-cell can be found in Basu S et al. (2010) (Basu S, Campbell H M, Dittel B N, Ray A. Purification of specific cell population by fluorescence activated cell sorting (FACS). J Vis Exp. (41): 1546) herein incorporated by reference in its entirety.

Formulation and Cryopreservation

In some embodiments, the engineered immune cells are formulated by first harvesting them from their culture medium, and then washing and concentrating the cells in a medium and container system suitable for administration (a "pharmaceutically acceptable" carrier) in a treatment-effective amount. Suitable infusion media can be any isotonic medium formulation, typically normal saline, Normosol™ R (Abbott) or Plasma-Lyte™ A (Baxter), but also 5% dextrose in water or Ringer's lactate can be utilized. The infusion medium can be supplemented with human serum albumin.

In another embodiment, the engineered immune cells, e.g., T cells expressing a CAR, are harvested, washed and concentrated and then cryopreserved at a predetermined cell concentration in a suitable cryopreservation medium, such as CryoStor® CS10, CryoStor® CS2 or CryoStor® CS5 (BioLife Solutions). Standard procedures are used for cryopreservation of engineered immune cells, e.g., T cells expressing the CAR, for storage and/or preparation for use in a human subject. When needed, the cryopreserved engineered immune cells can be thawed, grown and expanded to produce more of such cells.

Chimeric Antigen Receptors

As used herein, chimeric antigen receptors (CARs) are proteins that specifically recognize target antigens (e.g., target antigens on cancer cells). When bound to the target antigen, the CAR can activate the immune cell to attack and destroy the cell bearing that antigen (e.g., the cancer cell). CARs can also incorporate costimulatory or signaling domains to increase their potency. See, e.g., Finney et al., Journal of Immunology, 1998, 161: 2791-2797, Song et al., Blood 119:696-706 (2012); Kalas et al., Sci. Transl. Med. 3:95 (2011); Porter et al., N. Engl. J. Med. 365:725-33 (2011), and Gross et al., Annu. Rev. Pharmacol. Toxicol. 56:59-83 (2016); U.S. Pat. Nos. 7,741,465, and 6,319,494.

Chimeric antigen receptors described herein comprise an extracellular domain, a transmembrane domain, and an intracellular domain, wherein the extracellular domain comprises an antigen binding domain. In some embodiments, antigen specific CAR comprises the following elements from 5' to 3': a signal sequence, an antigen binding domain, a hinge and transmembrane region, and one or more successive signaling domains.

In some embodiments, the CARs further comprise a safety switch and/or monoclonal antibody specific epitope. See, e.g., WO2016/120216.

Antigen Binding Domain

As discussed above, the CARs described herein comprise an antigen binding domain. An "antigen binding domain" as used herein means any polypeptide that binds a specified target antigen. In certain embodiments, the polypeptide structure of the antigen binding domains is based on an antibody. Antigen binding domains include, but are not limited to, antibody binding regions that are immunologically functional fragments. The term "immunologically functional fragment" (or "fragment") of an antigen binding domain is a species of antigen binding domain comprising a portion (regardless of how that portion is obtained or synthesized) of an antibody that lacks at least some of the amino acids present in a full-length chain, but which is still capable of specifically binding to a target antigen. Such fragments are biologically active in that they bind to the target antigen and can compete with other antigen binding domains, including intact antibodies, for binding to a given epitope. Immunologically functional fragments include, but are not limited to, scFv fragments, Fab fragments (Fab', F(ab')2, and the like), one or more complementarity determining regions ("CDRs"), a diabody (heavy chain variable domain on the same polypeptide as a light chain variable domain, connected via a short peptide linker that is too short to permit pairing between the two domains on the same chain), domain antibodies, bivalent antigen binding domains (comprises two antigen binding sites), multi-specific antigen binding domains, and single-chain antibodies. These fragments can be derived from any mammalian source, including but not limited to human, mouse, rat, camelid or rabbit.

In some embodiments, antigen binding domains comprise one or more complementarity binding regions (CDRs) present in the full-length light or heavy chain of an antibody, and in some embodiments comprise a single heavy chain and/or light chain or portion thereof. These fragments can be produced by recombinant DNA techniques or can be produced by enzymatic or chemical cleavage of antigen binding domains, including intact antibodies.

In some embodiments, the antigen binding domain is an antibody of fragment thereof, including one or more of the complementarity determining regions (CDRs) thereof. In some embodiments, the antigen binding domain is a single chain variable fragment (scFv), comprising light chain CDRs CDR1, CDR2 and CDR3, and heavy chain CDRs CDR1, CDR2 and CDR3.

The assignment of amino acids to each of the framework, CDR, and variable domains is typically in accordance with numbering schemes of Kabat numbering (see, e.g., Kabat et al. in Sequences of Proteins of Immunological Interest, 5th Ed., NIH Publication 91-3242, Bethesda Md. 1991), Chothia numbering (see, e.g., Chothia & Lesk, (1987), J Mol Biol 196: 901-917; Al-Lazikani et al., (1997) J Mol Biol 273: 927-948; Chothia et al., (1992) J Mol Biol 227: 799-817; Tramontano et al., (1990) J Mol Biol 215(1): 175-82; and U.S. Pat. No. 7,709,226), contact numbering, or the AbM scheme (Antibody Modeling program, Oxford Molecular).

Variants of the antigen binding domains (e.g., variants of the CDRs, VH and/or VL) are also within the scope of the disclosure, e.g., variable light and/or variable heavy chains that each have at least 70-80%, 80-85%, 85-90%, 90-95%, 95-97%, 97-99%, or above 99% identity to the amino acid sequences of antigen binding domain sequences. In some instances, such molecules include at least one heavy chain and one light chain, whereas in other instances the variant forms contain two variable light chains and two variable heavy chains (or subparts thereof). A skilled artisan will be able to determine suitable variants of the antigen binding domains as set forth herein using well-known techniques. In certain some embodiments, one skilled in the art can identify suitable areas of the molecule that can be changed without destroying activity by targeting regions not believed to be important for activity.

In some embodiments, an antigen binding domain is a scFv. In some embodiments, an antigen-selective CAR comprises a leader or signal peptide. As will be appreciated by one of skill in the art, an antigen binding domain can include non-protein components.

Antigen binding domains suitable for use in a CAR in the methods and compositions of the instant disclosure can have a variety of antigen-binding specificities. In some embodiments, the antigen-binding domain is specific for an epitope present on an antigen that is expressed by (synthesized by) a target cell. In one example, the target cell is a cancer cell associated antigen. The cancer cell associated antigen can be an antigen associated with, e.g., a breast cancer cell, a B cell lymphoma, a Hodgkin lymphoma cell, an ovarian cancer cell, a prostate cancer cell, a mesothelioma, a lung cancer cell (e.g., a small cell lung cancer cell), a non-Hodgkin B-cell lymphoma (B-NHL) cell, an ovarian cancer cell, a prostate cancer cell, a mesothelioma cell, a lung cancer cell (e.g., a small cell lung cancer cell), a melanoma cell, a chronic lymphocytic leukemia cell, an acute lymphocytic leukemia cell, a neuroblastoma cell, a glioma, a glioblastoma, a medulloblastoma, a colorectal cancer cell, etc. A cancer cell associated antigen can also be expressed by a non-cancerous cell.

Non-limiting examples of antigens to which a chimeric binding antigen can bind include, e.g., CD19, CD20, CD38, CD30, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, Ax1, Ror2, BCMA. Claudin and its isotypes and the like.

Hinge Domain

The extracellular domain of the CARs of the disclosure can comprise a "hinge" domain (or hinge region). The term comprises any polypeptide that functions to link the transmembrane domain in a CAR to the extracellular antigen binding domain in a CAR. In particular, hinge domains can be used to provide more flexibility and accessibility for the extracellular antigen binding domain.

A hinge domain can comprise up to 300 amino acids—in some embodiments 10 to 100 amino acids or in some embodiments 25 to 50 amino acids. The hinge domain can be derived from all or part of naturally occurring molecules, such as from all or part of the extracellular region of CD8, CD4, CD28, 4-1BB, or IgG (in particular, the hinge region of an IgG; it will be appreciated that the hinge region can contain some or all of a member of the immunoglobulin family such an IgG1, IgG2, IgG3, IgG4, IgA, IgD, IgE, IgM, or fragment thereof), or from all or part of an antibody heavy-chain constant region.

Alternatively, the hinge domain can be a synthetic sequence that corresponds to a naturally occurring sequence or can be an entirely synthetic sequence. In some embodiments the hinge domain is a part of human CD8a chain (e.g., NP_001139345.1). In another particular embodiment, said hinge and transmembrane domains comprise a part of human CD8a chain. In some embodiments, the hinge domain of CARs described herein comprises a subsequence of CD8a, CD28, an IgG1, IgG4, PD-1 or an FcyRIIIa molecule, in particular the hinge region of any of CD8a, CD28, an IgG1, IgG4, PD-1 or an FcyRIIIa molecule. In some embodiments, the hinge domain comprises a human CD8a hinge, a human IgG1 hinge, a human IgG4 hinge, a human PD-1 hinge or a human FcyRIIIa hinge. In some embodiments the CARs disclosed herein comprise a scFv, CD8a human hinge and transmembrane domains.

Transmembrane Domain

CARs of the disclosure are designed with a transmembrane domain that is fused to the extracellular domain of the CAR. It can similarly be fused to the intracellular domain of the CAR. In some instances, the transmembrane domain can be selected or modified by amino acid substitution to avoid binding of such domains to the transmembrane domains of the same or different surface membrane proteins to minimize interactions with other members of the receptor complex. In some embodiments, short linkers can form linkages between any or some of the extracellular, transmembrane, and intracellular domains of the CAR. Suitable transmembrane domains for a CAR disclosed herein have the ability to (a) be expressed at the surface an immune cell such as, for example without limitation, a lymphocyte cell, such as a CD4+ cell such as a T helper (Th) cell, a CD8+ cell such as a cytotoxic T (Tc) cell, a T regulatory (Treg) cell, or a Natural Killer (NK) cell, and/or (b) interact with the extracellular antigen binding domain and intracellular signaling domain for directing the cellular response of an immune cell against a target cell.

The transmembrane domain can be derived either from a natural or from a synthetic source. Where the source is natural, the domain can be derived from any membrane-bound or transmembrane protein. Transmembrane regions of particular use in this disclosure can be derived from (comprise, or correspond to) CD28, CD8, OX-40, 4-1BB/CD137, CD2, CD7, CD27, CD30, CD40, programmed death-I (PD-1), inducible T cell costimulator (ICOS), lymphocyte function-associated antigen-I (LFA-1, CD1-la/CD18), CD3 gamma, CD3 delta, CD3 epsilon, CD247, CD276 (B7-H3), LIGHT, (TNFSF14), NKG2C, Ig alpha (CD79a), DAP-10, Fe gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptors, ICAM-1, B7-H3, CDS, ICAM-1, GITR, BAFFR, LIGHT, HVEM (LIGHTR), KIRDS2, SLAMF7, NKp80 (KLRFl), NKp44, NKp30, NKp46, CD19, CD4, CD8alpha, CD8beta, IL-2R beta, IL-2R gamma, IL-7R alpha, ITGA4, VLAl, CD49a, ITGA4, IA4, CD49D, ITGA6, VLA-6, CD49f, ITGAD, CDI ld, ITGAE, CD103, ITGAL, CDI la, LFA-1, ITGAM, CDI lb, ITGAX, CDI le, ITGBl, CD29, ITGB2, CD18, LFA-1, ITGB7, NKG2D, TNFR2, TRANCE/RANKL, DNAMl (CD226), SLAMF4 (CD244, 2B4), CD84, CD96 (Tactile), CEACAMl, CRT AM, Ly9 (CD229), CD160 (BY55), PSGL1, CD100 (SEMA4D), CD69, SLAMF6 (NTB-A, Lyl08), SLAM (SLAMFl, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

As non-limiting examples, the transmembrane region can be a derived from, or be a portion of a T cell receptor, polypeptide constituting CD3 complex, IL-2 receptor, p55 (a chain), p75 (P chain) or y chain, subunit chain of Fe receptors, in particular Fey receptor III or CD proteins. Alternatively, the transmembrane domain can be synthetic and can comprise predominantly hydrophobic residues such as leucine and valine. In some embodiments said transmembrane domain is derived from the human CD8a chain (e.g., NP_001139345.1).

Intracellular Domain

The intracellular (cytoplasmic) domain of the CARs of the disclosure can provide activation of at least one of the normal effector functions of the immune cell comprising the CAR, e.g., Signal 1/activation and/or Signal 2/costimulation. Effector function of a T cell, for example, can refer to cytolytic activity or helper activity, including the secretion of cytokines. In some embodiments, an activating intracellular signaling domain for use in a CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability.

It will be appreciated that suitable (e.g., activating) intracellular domains include, but are not limited to signaling domains derived from (or corresponding to) CD3 zeta, CD28, OX-40, 4-1BB/CD137, CD2, CD7, CD27, CD30, CD40, programmed death-I (PD-1), inducible T cell costimulator (ICOS), lymphocyte function-associated antigen-I (LFA-1, CD1-la/CD18), CD3 gamma, CD3 delta, CD3 epsilon, CD247, CD276 (B7-113), LIGHT, (TNFSF14), NKG2C, lg alpha (CD79a), DAP-10, Fe gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptors, ICAM-1, B7-H3, CDS, ICAM-1, GITR, BAFFR, LIGHT, HVEM (LIGHTR), KIRDS2, SLAMF7, NKp80 (KLRFl), NKp44, NKp30, NKp46, CD19, CD4, CD8alpha, CD8beta, IL-2R beta, IL-2R gamma, IL-7R alpha, ITGA4, VLAl, CD49a, ITGA4, IA4, CD49D, ITGA6, VLA-6, CD49f, ITGAD, CDI ld, ITGAE, CD103, ITGAL, CDI la, LFA-1, ITGAM, CDI lb, ITGAX, CDI le, ITGBl, CD29, ITGB2, CD18, LFA-1, ITGB7, NKG2D, TNFR2, TRANCE/RANKL, DNAMl (CD226), SLAMF4 (CD244, 2B4), CD84, CD96 (Tactile), CEACAMl, CRT AM, Ly9 (CD229), CD160 (BY55), PSGL1, CD100 (SEMA4D), CD69, SLAMF6 (NTB-A, Lyl08), SLAM (SLAMFl, CD150, IPO-3), BLAME (SLAMF8), SELPLG (CD162), LTBR, LAT, GADS, SLP-76, PAG/Cbp, CD19a, a ligand hat specifically binds with CD83, or any combination thereof An intracellular domain can incorporate, in addition to the activating domains described above, costimulatory signaling domains (interchangeably referred to herein as costimulatory molecules) to increase their potency. Costimulatory domains can provide a signal in addition to the primary signal provided by an activating molecule as described herein.

It will be appreciated that suitable costimulatory domains within the scope of the disclosure can be derived from (or correspond to) for example, CD28, OX40, 4-1BB/CD137, CD2, CD3 (alpha, beta, delta, epsilon, gamma, zeta), CD4, CDS, CD7, CD9, CD16, CD22, CD27, CD30, CD 33, CD37, CD40, CD 45, CD64, CD80, CD86, CD134, CD137, CD154, PD-1, ICOS, lymphocyte function-associated antigen-I (LFA-1 (CDI la/CD18), CD247, CD276 (B7-H3), LIGHT (tumor necrosis factor superfamily member 14; TNFSF14), NKG2C, lg alpha (CD79a), DAP-10, Fe gamma receptor, MHC class I molecule, TNFR, integrin, signaling lymphocytic activation molecule, BTLA, Toll ligand receptors, ICAM-1, B7-H3, CDS, ICAM-1, GITR, BAFFR, LIGHT, HVEM (LIGHTR), KIRDS2, SLAMF7, NKp80 (KLRFl), NKp44, NKp30, NKp46, CD19, CD4, CD8alpha, CD8beta, IL-2R beta, IL-2R gamma, IL-7R alpha, ITGA4, VLAl, CD49a, ITGA4, IA4, CD49D, ITGA6, VLA-6, CD49f, ITGAD, CDl-ld, ITGAE, CD103, ITGAL, CDl-la, LFA-1, ITGAM, CDl-lb, ITGAX, CDl-lc, ITGBl, CD29, ITGB2, CD18, LFA-1, ITGB7, NKG2D, TNFR2, TRANCE/RANKL, DNAMl (CD226), SLAMF4 (CD244, 2B4), CD84, CD96 (Tactile), CEACAMl, CRT AM, Ly9 (CD229), CD160 (BY55), PSGL1, CD100 (SEMA4D), CD69, SLAMF6 (NTB-A, Lyl08), SLAM (SLAMFl, CD150, IPO-3), BLAME (SLAMF8), SELPLG (CD162), LTBR, LAT, GADS, SLP-76, PAG/Cbp, CD19a, CD83 ligand, or fragments or combinations thereof. It will be appreciated that additional costimulatory molecules, or fragments thereof, not listed above are within the scope of the disclosure.

In some embodiments, the intracellular/cytoplasmic domain of the CAR can be designed to comprise the 4-1BB/CD137 domain by itself or combined with any other desired intracellular domain(s) useful in the context of the CAR. The complete native amino acid sequence of 4-1BB/CD137 is described in NCBI Reference Sequence: NP_001552.2. The complete native 4-1BB/CD137 nucleic acid sequence is described in NCBI Reference Sequence: NM 001561.5.

In some embodiments, the intracellular/cytoplasmic domain of the CAR can be designed to comprise the CD28 domain by itself or combined with any other desired intracellular domain(s) useful in the context of the CAR. The complete native amino acid sequence of CD28 is described in NCBI Reference Sequence: NP_006130.1. The complete native CD28 nucleic acid sequence is described in NCBI Reference Sequence: NM_006139.1.

In some embodiments, the intracellular/cytoplasmic domain of the CAR can be designed to comprise the CD3 zeta domain by itself or combined with any other desired intracellular domain(s) useful in the context of the CAR. In some embodiments, the intracellular signaling domain of the CAR can comprise the CD31 signaling domain. For example, the intracellular domain of the CAR can comprise a CD3 zeta chain portion and a portion of a costimulatory signaling molecule. The intracellular signaling sequences within the intracellular signaling portion of a CAR can be linked to each other in a random or specified order.

Nuclei Acid and Expression Vector Preparation

Provided herein are methods of making nucleic acid encoding a CAR and vectors comprising CAR-encoding nucleic acids.

A variety of known techniques can be utilized in making the polynucleotides and vectors according to the disclosure. For example, certain methods for making the constructs and engineered immune cells of the disclosure are described in disclosure WO2015/120096, the contents of which are hereby incorporated by reference in their entirety.

A nucleotide sequence encoding a CAR can be present in an expression vector. Where a CAR includes two separate polypeptides, nucleotide sequences encoding the two polypeptides can be cloned in the same or separate vectors. An expression vector can include a selectable marker, an origin of replication, and other features that provide for replication and/or maintenance of the vector. Suitable expression vectors include, e.g., plasmids, viral vectors, and the like.

For cloning of polynucleotides, an expression vector can be introduced into a host cell (an isolated host cell) to allow replication of the vector itself and thereby amplify the copies of the polynucleotide contained therein. The cloning vectors can contain sequence components generally include, without limitation, an origin of replication, promoter sequences, transcription initiation sequences, enhancer sequences, and selectable markers. These elements can be selected as appropriate by a person of ordinary skill in the art. For example, the origin of replication can be selected to promote autonomous replication of the vector in the host cell.

In other embodiments, the disclosure relates to isolated polynucleotides encoding any one of the antigen binding domains described herein. In some embodiments, the disclosure relates to isolated polynucleotides encoding a CAR.

Also provided herein are vectors comprising the polynucleotides, and methods of making same.

In certain embodiments, the present disclosure provides isolated host cells containing the expression vector provided herein. The host cells containing the vector can be useful in expression or cloning of the polynucleotide contained in the vector. Suitable host cells can include, without limitation, prokaryotic cells, fungal cells, yeast cells, or higher eukaryotic cells such as mammalian cells, and more specifically human cells.

The vector can be introduced to the host cell using any suitable methods known in the art, including, without limitation, DEAE-dextran mediated delivery, calcium phosphate precipitate method, cationic lipids mediated delivery, liposome mediated transfection, electroporation, microprojectile bombardment, receptor-mediated gene delivery, delivery mediated by polylysine, histone, chitosan, and peptides. Standard methods for viral transfection and transformation of cells for expression of a vector of interest are well known in the art. In a further embodiment, a mixture of different expression vectors can be used in genetically modifying a donor population of immune effector cells wherein each vector encodes a different CAR as disclosed herein. The resulting transduced immune effector cells form a mixed population of engineered cells, with a proportion of the engineered cells expressing more than one different CARs.

Retroviral Particle Preparation

In illustrative embodiments disclosed herein, the method of transduction can include a step of transducing immune cells, such as T cells, with replication incompetent recombinant retroviral particles comprising one or more nucleic acids to generate transduced, engineered immune cells such as engineered T cells. In some embodiments, the one or more nucleic acids can encode one or more proteins that are then expressed in the transduced T cells for example, a chimeric antigen receptor (CAR). The retroviral particles used to transduce the T cells and/or NK cells in the methods provided herein can be made according to methods known in the art. As disclosed herein, retroviral particles are a common tool for gene delivery (Miller, Nature (1992) 357:455-460). In some embodiments, the replication incompetent recombinant retroviral particles can be derived from the Alpharetrovirus genus, the Betaretrovirus genus, the Gammaretrovirus genus, the Deltaretrovirus genus, the Epsilonretrovirus genus, the Lentivirus genus, or the Spumavirus genus. There are many retroviruses suitable for use in the methods disclosed herein. A detailed list of retroviruses can be found in Coffin et al ("Retroviruses" 1997 Cold Spring Harbor Laboratory Press Eds: J M Coffin, S M Hughes, H E Varmus pp 758-763). Details on the genomic structure of some retroviruses can be found in the art. By way of example, details on HIV can be found from the NCBI Genbank (i.e., Genome Accession No. AF033819).

In illustrative embodiments, the retroviral particles can be derived from a recombinant retrovirus from the Lentivirus genus and can be replication incompetent recombinant lentiviral particles. In some embodiments, the recombinant retrovirus can be derived from HIV, SIV, or FIV. In further illustrative embodiments, the recombinant retrovirus can be derived from the human immunodeficiency virus (HIV) in the Lentivirus genus.

In some embodiments, the replication incompetent recombinant retroviral particles can be grown in a culture in a medium which is specific for replication incompetent recombinant retroviral particle manufacturing. Any suitable growth media and/or supplements for growing replication incompetent recombinant retroviral particles can be used in the replication incompetent recombinant retroviral particle inoculum in accordance with the methods described herein. According to some aspects, the retroviral particles can then be added to the media during the transduction steep.

The replication incompetent recombinant retroviral particles can be produced using mammalian cell lines according to methods known in the art. Suitable mammalian cells include primary cells and immortalized cell lines. Suitable mammalian cell lines can include human cell lines. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL1O), PC12 cells (ATCC No. CRL1721), COS cells, COS-7 cells (ATCC No. CRL1651), human embryonic kidney (HEK) cells (ATCC No. CRL1573), HLHepG2 cells, Hut-78, Jurkat, HL-60, NK cell lines (e.g., NKL, NK92, and YTS), and the like. In some instances, the cell is not an immortalized cell line, but is instead a cell (e.g., a primary cell) obtained from an individual or an ex vivo cell. For example, in some embodiments, the cell is an immune cell obtained from an individual. As another example, the cell is a stem cell or progenitor cell obtained from an individual.

Engineered Immune Cells

The engineered immune cells of the instant disclosure can be allogeneic or autologous.

In some embodiments, the engineered immune cell is a T cell (e.g., inflammatory T lymphocyte, cytotoxic T lymphocyte, regulatory T lymphocyte (Treg), helper T lymphocyte, tumor infiltrating lymphocyte (TIL)), natural killer T cell (NKT), TCR-expressing cell, dendritic cell, killer dendritic cell, a mast cell, natural killer cell or a B-cell. In some embodiments, the cell can be derived from the group comprising one or both of CD4+T-lymphocytes and CD8+T-lymphocytes. In some exemplary embodiments, the engineered immune cell is a T cell. In some exemplary embodiments, the engineered immune cell is a gamma delta T cell. In some exemplary embodiments, the engineered immune cell is a macrophage. In some exemplary embodiments, the engineered immune cell is a natural killer (NK) cell.

As described above, in some embodiments, the engineered immune cell can be derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. In some embodiments, the cell is obtained or prepared from peripheral blood. In some embodiments, the cell is obtained or prepared from peripheral blood mononuclear cells (PBMCs). In some embodiments, the cell is obtained or prepared from bone marrow. In some embodiments, the cell is obtained or prepared from umbilical cord blood. In some embodiments, the cell is a human cell.

In some embodiments, the immune cell is a T-lymphocyte that expresses a CAR produced by the methods described herein. In some embodiments, the immune cell is a cytotoxic T-lymphocyte that expresses a CAR produced by the methods described herein. In some embodiments, the immune cell is a regulatory T-lymphocyte that expresses a CAR produced by the methods described herein. In some embodiments, the immune cell is a helper T-lymphocyte that expresses a CAR produced by the methods described herein. In some embodiments, an engineered immune cell of the instant disclosure comprises a population of CARs, each CAR comprising different extracellular antigen-binding domains. In some embodiments, an immune cell comprises a population of CARs, each CAR comprising the same extracellular antigen-binding domains.

Also provided herein are cell lines obtained from a transformed immune cell (e.g., T-cell) according to any of the above-described methods. Also provided herein are modified cells resistant to an immunosuppressive treatment. In some embodiments, an isolated cell according to the disclosure comprises a polynucleotide encoding a CAR. In some embodiments, an engineered immune cell comprises a population of CARs, each CAR comprising an extracellular antigen-binding domain. In some embodiments, an immune cell comprises a population of CARs, each CAR comprising the same extracellular antigen-binding domains.

In some embodiments, an engineered immune cell according to the present disclosure can comprise one or more disrupted or inactivated genes. In some embodiments, an engineered immune cell according to the present disclosure comprises one disrupted or inactivated gene selected from the group consisting of CD52, DLL3, GR, PD-1, CTLA-4, LAG3, TIM3, BTLA, BY55, TIGIT, B7H5, LAIR1, SIGLEC10, 2B4, HLA, TCRa and TCRb and/or expresses a CAR, a multi-chain CAR and/or a pTa transgene. In some embodiments, an isolated cell comprises polynucleotides encoding polypeptides comprising a multi-chain CAR. In some embodiments, the isolated cell according to the present disclosure comprises two disrupted or inactivated genes selected from the group consisting of: CD52 and GR, CD52 and TCRa, CDR52 and TCRb, GR and TCRa, GR and TCRb, TCRa and TCRb, PD-1 and TCRa, PD-1 and TCRb, CTLA-4 and TCRa, CTLA-4 and TCRb, LAG3 and TCRa, LAG3 and TCRb, TIM3 and TCRa, Tim3 and TCRb, BTLA and TCRa, BTLA and TCRb, BY55 and TCRa, BY55 and TCRb, TIGIT and TCRa, TIGIT and TCRb, B7H5 and TCRa, B7H5 and TCRb, and TCRb, SIGLEC 10 and TCRa, SIGLEC 10 and TCRb, 2B4 and TCRa, 2B4 and TCRb and/or expresses a CAR, a multi-chain CAR and a pTa transgene.

In some embodiments, TCR is rendered not functional in the cells according to the disclosure by disrupting or inactivating TCRa gene and/or TCRβ gene(s). In some embodiments, a method to obtain modified cells derived from an individual is provided, wherein the cells can proliferate independently of the major histocompatibility complex (MHC) signaling pathway. Modified cells, which can proliferate independently of the MHC signaling pathway, obtainable by this method are encompassed in the scope of the present disclosure.

In some embodiments, the immune cells are engineered to be resistant to one or more chemotherapy drugs. The chemotherapy drug can be, for example, a purine nucleotide analogue (PNA), thus making the immune cell suitable for cancer treatment combining adoptive immunotherapy and chemotherapy. Exemplary PNAs include, for example, clofarabine, fludarabine, cyclophosphamide, and cytarabine, alone or in combination. PNAs are metabolized by deoxycytidine kinase (dCK) into mono-, di-, and triphosphate PNA. Their tri-phosphate forms compete with ATP for DNA synthesis, act as pro-apoptotic agents, and are potent inhibitors of ribonucleotide reductase (RNR), which is involved in trinucleotide production.

In some embodiments, isolated cells or cell lines of the disclosure can comprise a pTa or a functional variant thereof. In some embodiments, an isolated cell or cell line can be further genetically modified by disrupting or inactivating the TCRa gene.

As described above, the disclosure also provides engineered immune cells comprising a CAR polynucleotide. In some embodiments, a CAR can be introduced into an immune cell as a transgene via a plasmid vector. In some embodiments, the plasmid vector can also contain, for example, a selection marker which provides for identification and/or selection of cells which received the vector.

In some embodiments, the cell is transfected with nucleic acid vector of the instant disclosure using a method selected from the group consisting of electroporation, sonoporation, biolistics (e.g., Gene Gun), lipid transfection, polymer transfection, nanoparticles, or polyplexes. In some embodiments the cell is transduced with a viral vector of the instant disclosure, e.g., a retroviral vector, particularly a lentiviral vector.

Methods of Treatment

Methods are provided for treating diseases or disorders, including cancer. In some embodiments, the disclosure relates to creating a T cell-mediated immune response in a subject, comprising administering an effective amount of the engineered immune cells of the present instant disclosure to the subject. In some embodiments, the T cell-mediated immune response is directed against a target cell or cells. In some embodiments, the engineered immune cell comprises a chimeric antigen receptor (CAR). In some embodiments, the target cell is a tumor cell. In some aspects, the disclosure comprises a method for treating or preventing a malignancy, said method comprising administering to a subject in need thereof an effective amount of at least one isolated antigen binding domain described herein. In some aspects, the disclosure comprises a method for treating or preventing a malignancy, said method comprising administering to a subject in need thereof an effective amount of at least one immune cell, wherein the immune cell comprises at least one chimeric antigen receptor, and/or isolated antigen binding domain as described herein.

In some embodiments, the subject has a solid tumor, or a blood malignancy such as lymphoma or leukemia. In some embodiments, the cancer is present in the bone marrow of the subject. In some embodiments, the engineered cells are autologous immune cells, e.g., autologous T cells. In some embodiments, the engineered cells are allogeneic immune cells, e.g., allogeneic T cells. In some embodiments, the engineered cells are heterologous immune cells, e.g., heterologous T cells. In some embodiments, the engineered cells are transfected and/or transduced ex vivo. As used herein, the term "in vitro cell" refers to any cell that is cultured ex vivo. A "therapeutically effective amount," "effective dose," "effective amount," or "therapeutically effective dosage" of a therapeutic agent, e.g., engineered CART cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner (e.g., a physician or clinician), such as in human subjects during clinical trials, in animal model systems predictive of efficacy in humans, or by assaying the activity of the agent in in vitro assays.

The terms "patient" and "subject" are used interchangeably and include human subjects as well as those with formally diagnosed disorders, those without formally recognized disorders, those receiving medical attention, those at risk of developing the disorders, etc.

The term "treat" and "treatment" includes therapeutic treatments, prophylactic treatments, and disclosures in which one reduces the risk that a subject will develop a disorder or other risk factor. Treatment does not require the complete curing of a disorder and encompasses embodiments in which one reduces symptoms or underlying risk factors. The term "prevent" does not require the 100% elimination of the possibility of an event. Rather, it denotes that the likelihood of the occurrence of the event has been reduced in the presence of the compound or method.

Desired treatment total amounts of cells in the composition comprise at least 2 cells (for example, at least one CD8+ T cell and at least one CD4+ T cell, or two CD8+ T cells, or two CD4+ T cells) or is more typically greater than $10^2$ cells, and up to $10^6$, up to and including $10^8$ or $10^9$ cells and can be $10^{10}$ or $10^{12}$ or more cells. The number of cells will depend upon the desired use for which the composition is intended, and the type of cells included therein. The density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present disclosure, particularly since all the infused cells will be redirected to a particular target antigen, lower numbers of cells, in the range of $10^6$/kilogram ($10^6$-$10^{11}$ per patient) can be administered. CAR treatments can be administered multiple times at dosages within these ranges.

The cells can be autologous, allogeneic, or heterologous to the patient undergoing therapy.

In some embodiments, the therapeutically effective amount of the CAR T cells is about $1\times10^5$ cells/kg, about $2\times10^5$ cells/kg, about $3\times10^5$ cells/kg, about $4\times10^5$ cells/kg, about $5\times10^5$ cells/kg, about $6\times10^5$ cells/kg, about $7\times10^5$ cells/kg, about $8\times10^5$ cells/kg, about $9\times10^5$ cells/kg, $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

In some embodiments, target doses for CAR+/CAR-T+ cells range from about $1\times10^6$ to about $1\times10^{10}$ cells/kg, for example about $1\times10^6$ cells/kg, about $1\times10^7$ cells/kg, about $1\times10^8$ cells/kg, about $1\times10^9$ cells/kg or about $1\times10^{10}$ cells/kg. It will be appreciated that doses above and below this range can be appropriate for certain subjects, and appropriate dose levels can be determined by the healthcare provider as needed. Additionally, multiple doses of cells can be provided in accordance with the disclosure.

In some aspects, the disclosure comprises a pharmaceutical composition comprising at least one antigen binding domain as described herein and a pharmaceutically acceptable excipient. In some embodiments, the pharmaceutical composition further comprises an additional active agent.

The CAR expressing cell populations of the present disclosure can be administered either alone, or as a pharmaceutical composition in combination with diluents and/or with other components such as IL-2 or other cytokines or cell populations. Pharmaceutical compositions of the present disclosure can comprise a CAR expressing cell population, such as T cells, as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

The pharmaceutical compositions (solutions, suspensions or the like), can include one or more of the following: sterile diluents such as water for injection, saline solution, preferably physiological saline, Ringer's solution, isotonic sodium chloride, fixed oils such as synthetic mono- or diglycerides which can serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. The parenteral preparation can be enclosed in ampoules, disposable syringes or multiple dose vials made of glass or plastic. For therapeutic disclosures, an injectable pharmaceutical composition is preferably sterile The methods can further comprise administering one or more chemotherapeutic agents to a patient prior to administering the engineered cells provided herein. In certain embodiments, the chemotherapeutic agent is a lymphodepleting (preconditioning) chemotherapeutic. For example, methods of conditioning a patient in need of a T cell therapy comprising administering to the patient specified beneficial doses of cyclophosphamide (between 200 mg/m2/day and 2000 mg/m2/day, about 100 mg/m2/day and about 2000 mg/m2/day; e.g., about 100 mg/m2/day, about 200 mg/m2/day, about 300 mg/m2/day, about 400 mg/m2/day, about 500 mg/m2/day, about 600 mg/m2/day, about 700 mg/m2/day, about 800 mg/m2/day, about 900 mg/m2/day, about 1000 mg/m2/day, about 1500 mg/m2/day or about 2000 mg/m2/day) and specified doses of fludarabine (between 20 mg/m2/day and 900 mg/m2/day, between about 10 mg/m2/day and about 900 mg/m2/day; e.g., about 10 mg/m2/day, about 20 mg/m2/day, about 30 mg/m2/day, about 40 mg/m2/day, about 40 mg/m2/day, about 50 mg/m2/day, about 60 mg/m2/day, about 70 mg/m2/day, about 80 mg/m2/day, about 9020 mg/m2/day, about 100 mg/m2/day, about 500 mg/m2/day or about 900 mg/m2/day). An exemplary dosing regimen involves treating a patient comprising administering daily to the patient about 300 mg/m2/day of cyclophosphamide in combination or before or after administering about 30 mg/m2/day of fludarabine for three days prior to administration of a therapeutically effective amount of engineered T cells to the patient.

In some embodiments, notably in the case when the engineered cells provided herein have been gene edited to eliminate or minimize surface expression of CD52, lymphodepletion further comprises administration of an anti-CD52 antibody, such as alemtuzumab. In some embodiments, the CD52 antibody is administered at a dose of about 1-20 mg/day IV, e.g., about 13 mg/day IV for 1, 2, 3, 4, 5, 6, 7 or more days.

The antibody can be administered in combination with, before, or after administration of other elements of a lymphodepletion regime (e.g., cyclophosphamide and/or fludarabine).

In other embodiments, the antigen binding domain, transduced (or otherwise engineered) cells and the chemotherapeutic agent are administered each in an amount effective to treat the disease or condition in the subject.

In certain embodiments, compositions comprising CAR-expressing immune effector cells disclosed herein can be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2', 2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RF S2000; difluoromethylomithine (DMFO); retinoic acid derivatives such as Targretin™ (bexarotene), Panretin™, (alitretinoin); ONT AK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)- imidazoles, 4-hydroxytamoxifen, trioxifene, keoxifene, LY1 17018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell, polypeptide, or nucleic acid. In other embodiments, the chemotherapeutic agent is administered from about 1-7 days, about 1 to about 4 weeks or from about 1 week to about 1 month, about 1 week to about 2 months, about 1 week to about 3 months, about 1 week to about 6 months, about 1 week to about 9 months, or about 1 week to about 12 months after the administration of the engineered cell, polypeptide, or nucleic acid. In other embodiments, the chemotherapeutic agent is administered at least 1 month before administering the cell, polypeptide, or nucleic acid. In some embodiments, the methods further comprise administering two or more chemotherapeutic agents.

A variety of additional therapeutic agents can be used in conjunction with the compositions described herein. For example, potentially useful additional therapeutic agents include PD-1 inhibitors such as nivolumab (Opdivo®), pembrolizumab (Keytruda®), pembrolizumab, pidilizumab, and atezolizumab. Additional therapeutic agents suitable for use in combination with the disclosure include, but are not limited to, ibrutinib (Imbruvica®), ofatumumab (Arzerra®, rituximab (Rituxan®), bevacizumab (Avastin®), trastuzumab (Herceptin®), trastuzumab emtansine (KADCYLA®, imatinib (Gleevec®), cetuximab (Erbitux®, panitumumab) (Vectibix®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In some embodiments, the composition comprising CAR-expressing immune cells can be administered with a therapeutic regimen to prevent or reduce cytokine release syndrome (CRS) or neurotoxicity. The therapeutic regimen to prevent cytokine release syndrome (CRS) or neurotoxicity can include lenzilumab, tocilizumab, atrial natriuretic peptide (ANP), anakinra, iNOS inhibitors (e.g., L-NIL or 1400W). In additional embodiments, the composition comprising CAR-containing immune cells can be administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, ethylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CDS, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

In certain embodiments, the compositions described herein are administered in conjunction with a cytokine. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-lalpha, IL-2, IL-3, IL-4, IL-5, IL-6, IL-7, IL-8, IL-9, IL-10, IL-11, IL-12; IL-15, IL-21 a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

Kits and Articles of Manufacture

The present disclosure provides kits comprising any one of the immune cells expressing a CAR using the methods provided herein, and pharmaceutical compositions of the same. In an embodiment of a kit, the engineered CAR cells are frozen in a suitable medium, such as CryoStor® CS10, CryoStor® CS2 or CryoStor® CS5 (BioLife Solutions).

In some exemplary embodiments, a kit of the disclosure comprises allogeneic CAR-expressing T-cells and a CD52 antibody for administering to the subject as a component of a lymphodepletion regiment and a CAR-T regimen. The present disclosure also provides articles of manufacture comprising any one of the therapeutic compositions or kits described herein. Examples of an article of manufacture include vials (e.g., sealed vials comprising an immune cell expressing a CAR).

EXAMPLES

Example 1: Effect of Process Factors on Immune Cell Transduction Efficiency

A. Effect of MOI, Growth Media pH, RetroNectin® Concentration and Culture Vessel on Percentage of Viable CAR 1+ Immune Cells PBMC Collection Donor blood was collected and separated into its component parts by apheresis. PBMCs were then enriched over a GE Ficoll©-plaque (density 1.077 g/mL) step gradient and cryopreserved in a buffer comprising 5% DMSO.

Activation

On Day 0, the Ficoll®-isolated frozen human PBMCs were thawed and washed one time with wash medium comprising X-VIVO™ 15 culture media (Lonza Biosciences) plus 10% human serum (Gemini Bio Products, Sacramento, CA). The cells were then cultured in culture media (also referred to herein as growth media) comprising X-VIVO™ 15 culture media (Lonza Biosciences) with 5% human serum (Gemini Bio Products, Sacramento, CA)) and incubated at 37° C. and 5% $CO_2$ overnight in a standard humidified tissue culture incubator. On Day 1, the cells were washed with wash medium, counted and resuspended in culture medium at a cell density of $1.5 \times 10^6$ per mL and mixed with T Cell TransAct™ polymeric nanomatrix (Miltenyi Biotec) at a volumetric dilution of 1:10. Recombinant human IL-2 (Miltenyi Biotec) was added to a final concentration of 100 U/mL. The T cells were then incubated at 37° C. and 5% $CO_2$ in a standard humidified tissue culture incubator until Day 4.

Transduction and Expansion

On Day 4, the cells were washed and resuspended in culture medium containing recombinant human IL-2 (Miltenyi Biotec) at a cell density of $1 \times 10^6$ per mL. The cells were transduced with a lentiviral vector (LVV #1831P, Lentigen Technology, Inc., Gaithersburg, Maryland) encoding CAR 1 (1560 nucleotides) under the test conditions described in Table 1 below and incubated at 37° C. and 5% $CO_2$ in a standard humidified tissue culture incubator until Day 6. On Day 6, the transduced cells were cultured to expand the cell population.

TABLE 1

| Test Group | % LVV (v/v) | MOI*** | Growth Media pH | RetroNectin® reagent Conc. (μg/mL) | Culture Vessel |
|---|---|---|---|---|---|
| 1 | .25 | 7.25 | 7.4 | 45.0 | Bag* |
| 2 | 10 | 290.0 | 7 | 45.0 | Bag |
| 3 | 5 | 145.0 | 7 | 22.5 | Bag |
| 4 | .25 | 7.25 | 6.6 | 22.5 | Bag |
| 5 | 5 | 145.0 | 7 | 22.5 | Bag |
| 6 | 5 | 145.0 | 7.4 | 0 | Bag |
| 7 | 10 | 290.0 | 6.6 | 0 | Bag |
| 8 | .25 | 7.25 | 6.6 | 45.0 | Well** |
| 9 | 10 | 290.0 | 7.4 | 45.0 | Well |
| 10 | 10 | 290.0 | 6.6 | 45.0 | Well |
| 11 | 5 | 145.0 | 7 | 22.5 | Well |
| 12 | 10 | 290.0 | 7.4 | 0 | Well |
| 13 | .25 | 7.25 | 7.4 | 0 | Well |
| 14 | .25 | 7.25 | 6.6 | 0 | Well |

*Culture bags are MACS Cell Differentiation Bags -100 (Miltenyi Biotec)
**Plates are 6 well culture plates (Corning, Inc.)
***Calculated from second column % LVV (v/v)

Transduction Efficiency Assessment

On Day 8 and 11, the transduction efficiency and cell viability were confirmed by flowcytometry. No polybrene, protamine sulfate or DEAE-dextran was added before, during or after the transduction. For each test group, a cell sample was washed and resuspended in dulbecco's phosphate buffered saline ("DPBS"). Two antibody/stain cocktails, each comprising a different panel of antibodies, were prepared using commercially available antibody/stain combinations.

About $1 \times 10^6$ cells from each test group sample was added to a FACS tube along with an aliquot of one of the antibody/stain cocktails. The FACS tubes were then incubated at 25° C. in the dark for 25±5 minutes. The samples were washed twice and resuspended in 1% Paraformaldehyde ("PFA") and then processed by a LSRFortessa cytometer (BD Biosciences, Franklin Lakes, New Jersey) and the resulting data was analyzed using FlowJo software Version 10 (FlowJo, LLC., Ashland, Oregon).

Table 2 below provides the % viable CAR+ T-cells for each test group on Day 8 and Day 11 of the study

TABLE 2

| Test Group | Day 8 | Day 11 |
|---|---|---|
| 1 | 22.6 | 42.9 |
| 2 | 46.7 | 73.4 |
| 3 | 48.0 | 76.4 |
| 4 | 10.8 | 32.7 |
| 5 | 42.6 | 75.8 |
| 6 | 56.1 | 66.0 |
| 7 | 13.4 | 25.7 |
| 8 | 12.7 | 21.6 |
| 9 | 52.7 | 69.6 |
| 10 | 26.2 | 43.8 |
| 11 | 52.0 | 65.6 |
| 12 | 53.6 | 65.3 |
| 13 | 14.8 | 22.7 |
| 14 | 10.0 | 18.3 |

The effects of the manufacturing process factors; % lentiviral vector (v/v), growth media pH, RetroNectin® reagent concentration and culture vessel on transduction efficiency, are illustrated in FIG. 2. The significance of main effects and interactions were determined by Analysis of Variance (ANOVA) with probability value (p-value) threshold set at <0.05 using JMP®14 software (SAS Institute, Inc., Cary, N.C.). Transducing the cells at a pH of 7.0 and higher resulted in greater percentage of viable CAR+ cells (see, FIG. 2A) than transducing the cells at a lower pH which resulted in a lower percentage of viable CAR+ cells (see, FIG. 2B). P-values for the main effects and 2-way interactions are shown in FIG. 2C.

As FIG. 2 illustrates, surprisingly, RetroNectin® reagent (Takara Bio USA) concentration does not have a significant effect on CAR transduction efficiency. Rather, pH has the most significant effect on transduction efficiency of all the factors tested with MOI and transduction vessel also contributing to transduction efficiency.

B. Effect of Growth Media pH and RetroNectin® Concentration on Percentage of Viable CAR-2+ Immune Cells PBMCs were collected, activated and CAR-2 (about 1500 nucleotides) was transduced by the methods described in Example 1A above in a partial factorial experiment (using JMPO 14 software, D-optimal design) to assess the effect of pH and RetroNectin® concentration on % Viable CAR-2+ T-cells.

Transduction Efficiency Assessment

On day 15, the transduction efficiency and cell viability were confirmed by flowcytometry as described in Example 1A above. The significance of main effects and interactions were determined and modeled by Analysis of Variance (ANOVA) with the probability value (p-value) threshold set at <0.05 using JMP® 14 software (SAS Institute, Inc., Cary, N.C.). The % viable CAR+ T-cells results were simulated using JMP® 14 ANOVA software at an MOI of 48 to assess the main effects of RetroNectin® and media pH on % viable CAR+ T-cells, at the RetroNectin® concentrations and media pH levels indicated in Table 3. The results are shown in the right-most column of Table 3.

TABLE 3

| Growth Media pH | RetroNectin ® reagent Conc. (µg/cm²) | % Viable CAR+ T-Cells |
|---|---|---|
| 7.3 | 0 | 70.8 |
| 7.3 | 15 | 79.8 |
| 6.7 | 0 | 50.1 |
| 6.7 | 15 | 55.5 |

Table 3 shows that transducing the T-cells at a pH of 7.3, resulted in greater percentage of viable CAR+ cells, both with or without RetroNectin® reagent, than transducing the cells at a lower pH of 6.7 both with and without RetroNectin® reagent. Surprisingly, RetroNectin® reagent concentration does not have the largest effect on CAR transduction efficiency. Media pH during transduction has the largest effect on transduction efficiency.

Example 2: Vector Integration Transduction Time Course

On Day 0, PBMCs (collected as described in Example 1 above) were thawed in a 2 L gas permeable bag (Xuri™ Cell Bag™, GE Lifesciences, Inc.) The cells, at a concentration of $1.5 \times 10^6$ cells/mL in X-VIVO™ 15 culture media (Lonza Biosciences) further comprising 5% human serum (Gemini Bio Products, Sacramento, CA), IL-2 and glutamine, were activated by adding TransAct™ polymeric nano matrix (Miltenyi Biotec) at a volumetric dilution of 1:10. The cells were cultured in a in wave action bioreactor at 37° C.

On Day 2, 1% (v/v) lentiviral vector (LVV #1831P, Lentigen Technology, Inc., Gaithersburg, Maryland) encoding CAR-2 (1500 nucleotides), was added to the cell culture at a pH of 7.2±0.1. The resulting transduction reaction mixture was cultured for 8 hours at 37° C. No RetroNectin® was used during the transduction. And no polybrene, protamine sulfate or DEAE-dextran was added before, during or after the transduction.

A cell sample was taken from the culture medium at 1, 2-, 4-, 6- and 8-hours post introduction of the lentiviral vector to the cells. Each cell sample was centrifuged, washed and resuspended in culture media at a cell density of $1 \times 10^6$ cells/mL and cultured in a G-Rex® cell culture system (Wilson Wolf Corporation, Saint Paul, Minnesota) at a volume of 40 mL for 14 days according to the manufacturer's instructions.

Percent CAR+ cells was determined on Day 7 and Day 14 by flow cytometry as described in Example 1 above.

Figure 3:
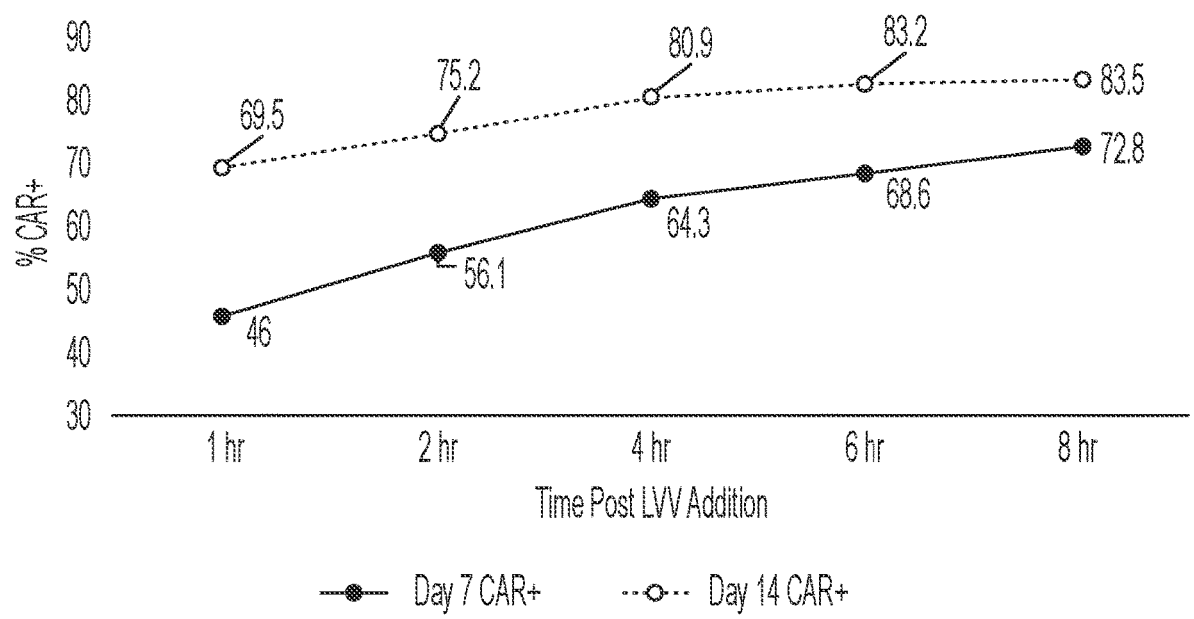
FIG. 3 shows the effect of 1, 2-, 4-, 6- and 8-hour transduction times (horizontal axis) carried out a pH of 7.2±0.1, on the percentage of CAR+ T cells (vertical axis) on Day 7 and Day 14 of the study.

The results are illustrated in FIG. 3. As illustrated by the figure, the % CAR+ cells are higher for every transduction time point on Day 14 as compared to Day 7. Further, on Day 14, the increase in % CAR+ cells begins to slow after 4 hours of transduction and begins to level off at 6 to 8 hours of transduction.

Example 3: Manufacturing Scale Immune Cell Transduction

Fourteen manufacturing scale runs for T-cells expressing CAR-1 were conducted. Runs 7-14 were carried out as described below. Runs 1-6 were conducted as described below with the one exception that the transducing step was carried out at pH lower than 7.2.

PBMC Collection, Activation and Transduction

PBMCs (collected as described in Example 1 above) were thawed in media comprising human serum, in a gas permeable bag and incubated overnight at 37° C. and 5% $CO_2$.

The PBMCs were then washed, resuspended in media comprising 5% human serum, IL-2, glutamine, CD3 and CD28 stimulating reagents and incubated at 37° C. and 5% $CO_2$.

The activated cells were washed with media to remove the activation reagents and resuspended in culture media. The cultured media comprised 5% human serum, TL-2 and glutamine. Prior to introducing the cells into the culture media, $CO_2$ was removed from the culture media to achieve a pH of 7.2 or greater. The cells were resuspended in a manufacturing scale volume of culture media (a manufacturing scale transduction volume) in a gas permeable bag at a cell density of $1 \times 10^6$ cells per mL. A lentiviral vector (LVV #1831P, Lentigen Technology, Inc., Gaithersburg, Maryland) encoding CAR-1 was added to the cell suspension at 10% LVV (V/V). The resulting transduction reaction mixture was cultured for 48 hours at 37° C. and 5% $CO^2$. No RetroNectin® was used during the transduction. And no polybrene, protamine sulfate or DEAE-dextran was added to the transduction.

Expansion

The cells were further electroporated to disrupt target genes and subsequently expanded in a perfusion wave bioreactor in a total volume of 1 liter of culture media. Enrichment of T cells was performed on Day 18 to select for T cells with disrupted gene expression.

CAR Expression and Cell Viability

On Day 19 CAR expression and cell viability were assessed by flow cytometry as described in Example 1A above and are described in Table 4 below.

TABLE 4

| Media pH <7.1 | | Media pH >7.1 | |
|---|---|---|---|
| Run # | % Viable CAR T Cells | Run # | % Viable CAR T Cells |
| 1 | 55.1 | 7 | 76.6 |
| 2 | 34.3 | 8 | 76.6 |
| 3 | 36.6 | 9 | 70.7 |
| 4 | 62.3 | 10 | 65.9 |
| 5 | 26 | 11 | 60.1 |
| 6 | 21.8 | 12 | 48.5 |
| | | 13 | 42.8 |
| | | 14 | 56.5 |
| Average | 39.4 | Average | 62.2 |
| STD* | 16.1 | STD | 12.5 |

*Standard Deviations

Table 4 shows that cells transduced at a pH of greater than 7.1 have a higher percentage of viable CAR expressing cells as compared to cells transduced at a pH less than 7.1. Further, the table shows that transducing the cells at a pH greater than 7.1 resulted in a more consistent percentage of viable CAR expressing cells, run to run, versus cells transduced at a pH of less than 7.1.

What is claimed is:

1. A method for transducing a population of human cells with a retroviral vector, the vector comprising a nucleic acid exogenous to the cells, the method comprising:
   culturing the population of human cells with the retroviral vector, in a cell culture media at a starting pH in a starting pH range of 7.0 to 7.4 and maintaining the starting pH in the starting pH range for at least a first hour of the transduction culturing step to result in a transduced cell population comprising cells expressing a gene product encoded by the exogenous nucleic acid, wherein the population of human cells are T lymphocytes, helper T cells, memory T cells, cytotoxic T cells, natural killer T cells, peripheral blood lymphocytes, peripheral blood mononuclear cells, dendritic cells, T cells derived from induced pluripotent stem cells, natural killer cells or mixtures thereof.

2. The method according to claim 1, wherein the starting pH is maintained in the starting pH range for at least about 1, about 2, about 4, about 6, about 8, about 10, about 12, about 14, about 16, about 18, about 20, about 22, about 24, about 36, about 48, about 72 or about 96 hours to no more than about 168 hours.

3. The method according to claim 1, wherein the starting pH is maintained above about 7.0 or is maintained in the starting pH range through the end of the transduction culturing step.

4. The method according to claim 3, wherein the transduction culturing step is conducted for at least about 1, about 2, about 4, about 6, about 8, about 12, about 14, about 16, about 18, about 20, about 22, about 24, about 36, about 48, about 72 or about 96 hours.

5. The method according to claim 1, wherein the cell culture media does not comprise a co-localization agent.

6. The method according to claim 1, wherein the cell culture media does not comprise fibronectin or a fibronectin derivative.

7. The method according to claim 1, wherein the cell population is cultured at a MOI of about 0.25, about 0.5, about 1, about 5, about 10, about 15, about 20, about 25, about 30, about 35, about 40, about 45, about, or about 50 to about 55, about 60, about 65, about 70, about 75, about 80, about 85, about 90, about 95, about 100, about 125, about 150, about 175, about 200, about 225, or about 250.

8. The method according to claim 1, wherein the exogenous nucleic acid encodes a chimeric antigen receptor.

9. The method according to claim 1, wherein the cell population is cultured in a vessel, wherein the vessel is a cell culture plate, cell culture deep well plate, a cell stack, a controlled bioreactor, a shake flask or a gas permeable bag.

10. The method according to claim 1, wherein the retroviral vector is a lentiviral vector.

11. The method according to claim 1, wherein the transduction culturing step comprises culturing the cell population and the retroviral vector in a volume of about 0.5 liters to a volume of about 10 liters of cell culture media.

12. The method according to claim 1, wherein, at least about 35% to about 95%, about 40% to about 95%, about 50% to about 95%, about 60% to about 95%, or about 70% to about 95%, of the transduced cell population expresses the exogenous nucleic acid gene product about 3 to about 18 days after initiation of the transduction culturing step.

13. The method according to claim 1, wherein, at least about 35% to about 95%, about 40% to about 95%, about 50% to about 95%, about 60% to about 95%, or about 70% to about 95%, of the transduced cell population expresses the exogenous nucleic acid gene product about 7 to about 18 days after initiation of the transduction culturing step.

14. The method according to claim 1, wherein the starting pH range is maintained passively.

15. The method according to claim 1, wherein the starting pH range is maintained actively.

16. The method according to claim 1, wherein the cell population is an allogeneic cell population.

17. The method according to claim 1, wherein the cell population is an autologous cell population.

18. A method for transducing a first and a second cell population, wherein the first and second cell population are transduced by the method of claim 1, whereby the percent of the transduced cell population expressing the exogenous nucleic acid gene product in the first and second transduced cell populations does not vary more than about 2% to about 5%, about 5% to about 10%, about 10% to about 20%, or about 20% to about 30%.

19. The method according to claim 1, wherein a polycation is not added to the cell culture media.

20. The method according to claim 1, wherein polybrene, protamine sulfate or DEAE-dextran is not added to the culture media.

21. The method according to claim 1, wherein fibronectin or a fibronectin derivative is not added to the cell culture media.

22. The method of claim 1, wherein the starting pH is 7.1, 7.2, 7.3 or 7.4.

23. A method for transducing a population of human cytotoxic T cells or human peripheral blood mononuclear cells with a retroviral vector, the vector comprising a nucleic acid exogenous to the cytotoxic T cells, the method comprising culturing the human cytotoxic T cell population or the human peripheral blood mononuclear cell population with the retroviral vector, in a cell culture media at a starting pH in a starting pH range of 7.0 to 7.4 and maintaining the starting pH in the starting pH range for at least a first hour of the transduction culturing step to result in a transduced cytotoxic T cell population or a transduced peripheral blood mononuclear cell population comprising cells expressing the gene product encoded by the exogenous nucleic acid, wherein the cell culture media does not comprise a co-localization agent.

24. The method according to claim 23, wherein the cell culture media does not comprise fibronectin or a fibronectin derivative.

25. The method of claim 23, wherein the starting pH is maintained actively.

26. The method of claim 23, wherein the starting pH is 7.1, 7.2, 7.3 or 7.4.

27. A method for transducing a population of human T cells derived from induced pluripotent stem cells with a retroviral vector, the vector comprising a nucleic acid exogenous to the derived T cells, the method comprising culturing the derived T cell population with the retroviral vector, in a cell culture media at a starting pH in a starting pH range of 7.0 to 7.4 and maintaining the starting pH in the starting pH range for at least a first hour of the transduction culturing step to result in a transduced derived T cell population comprising cells expressing the gene product encoded by the exogenous nucleic acid, wherein the cell culture media does not comprise a co-localization agent.

28. The method of claim 27, wherein the starting pH is maintained actively.

29. The method of claim 27, wherein the starting pH is 7.1, 7.2, 7.3 or 7.4.

* * * * *